(12) United States Patent
Wang et al.

(10) Patent No.: US 11,953,495 B1
(45) Date of Patent: Apr. 9, 2024

(54) MOLECULAR DETECTION UNIT, CHIP AND PREPARATION METHOD

(71) Applicant: Beijing Qitan Tech Co., Ltd., Beijing (CN)

(72) Inventors: Yuan Wang, Beijing (CN); Xiaoxiang Xia, Beijing (CN); Lu Song, Beijing (CN)

(73) Assignee: Beijing Qitan Tech Co., Ltd., Beijing (CN)

( * ) Notice: Subject to any disclaimer, the term of this patent is extended or adjusted under 35 U.S.C. 154(b) by 0 days.

(21) Appl. No.: 18/470,619

(22) Filed: Sep. 20, 2023

(30) Foreign Application Priority Data

Dec. 7, 2022 (CN) .......................... 202211566764.8

(51) Int. Cl.
*G01N 33/487* (2006.01)
(52) U.S. Cl.
CPC ............................. *G01N 33/48721* (2013.01)
(58) Field of Classification Search
None
See application file for complete search history.

(56) References Cited

U.S. PATENT DOCUMENTS

| | | | |
|---|---|---|---|
| 10,473,639 B1 | 11/2019 | Turner et al. | |
| 2021/0139974 A1* | 5/2021 | So | B32B 37/18 |
| 2021/0154665 A1* | 5/2021 | Ikeda | G01N 27/128 |
| 2022/0074920 A1 | 3/2022 | Todd et al. | |
| 2022/0221441 A1* | 7/2022 | Heron | G01N 33/48721 |
| 2023/0103446 A1* | 4/2023 | Choy | B01L 3/5027 |
| | | | 204/403.01 |
| 2023/0349882 A1* | 11/2023 | Xie | G01N 15/1245 |

FOREIGN PATENT DOCUMENTS

| | | |
|---|---|---|
| CN | 104254619 A | 12/2014 |
| CN | 106010949 A | 10/2016 |
| CN | 110366680 A | 10/2019 |

OTHER PUBLICATIONS

First Office Action issued in counterpart Chinese Patent Application No. 202211566764.8, dated Feb. 1, 2023.

* cited by examiner

*Primary Examiner* — Samuel C Woolwine
(74) *Attorney, Agent, or Firm* — Westbridge IP LLC

(57) ABSTRACT

Disclosed are a molecule detection unit, a chip and a preparation method. The molecule detection unit includes a single-hole liquid storage cavity, a liquid resistance flow channel, a buffer flow channel, a sensing electrode, a substrate, a first structural layer, a second structural layer and a sample flow channel. The first structural layer is arranged on the top of the substrate; the single-hole liquid storage cavity and the buffer flow channel are arranged in the first structural layer and are independent of each other; the liquid resistance flow channel is arranged in the first structural layer, and two ends of the liquid resistance flow channel are respectively communicated with the single-hole liquid storage cavity and the buffer flow channel; the second structural layer is arranged on the top of the first structural layer and covers the top of the buffer flow channel.

20 Claims, 28 Drawing Sheets

MOLECULAR DETECTION UNIT, CHIP AND PREPARATION METHOD

CROSS-REFERENCE TO RELATED APPLICATIONS

This application claims priority to Chinese Patent Application No. CN202211566764.8, filed on Dec. 7, 2022, which is hereby incorporated by reference in its entirety.

TECHNICAL FIELD

The present application relates to the technical field of biological detection, in particular to a molecular detection unit, a chip and a preparation method thereof.

BACKGROUND ART

A nanopore sequencing device is a device that determines the base pair sequence of a DNA molecule by detecting the change in the electrical signal generated when the DNA molecule passes through a nanometer-sized hole. This type of device generally consists of a membrane that separates two liquid storage cavities and a nanopore embedded in the membrane.

In the prior art, the liquid resistance flow channel and the buffer flow channel in the above-mentioned nanopore sequencing device are usually realized by making through-holes in the substrate. Therefore, the liquid storage cavity and the buffer flow channel will be respectively located on two sides of the substrate.

However, in the field of micro-nano processing technology, the commonly used methods of making through-holes have certain requirements on the thickness of the material and the geometric shape of the through-holes. At present, most nanopore sequencing devices are manufactured based on silicon wafers, and their thickness is mostly several hundred micrometers, while the diameter of the through-holes required in nanopore sequencing devices is often in the range of several micrometers. In the prior art, due to factors such as load effect and mask layer area, relatively mature high aspect ratio micro-nano processing technology can only effectively complete deep hole etching with an maximum aspect ratio of 15:1 in actual production. Therefore, how to effectively fabricate this type of through-substrate structure has become an important factor restricting the fabrication and mass production of nanopore sequencing devices.

SUMMARY

Embodiments of the present disclosure provide a molecular detection unit, a chip and a preparation method.

In a first aspect, an embodiment of the present disclosure provides a molecular detection unit, which including: a single-hole liquid storage cavity, a liquid resistance flow channel, a buffer flow channel, a sensing electrode, a substrate, a first structural layer, a second structural layer, and a sample flow channel; wherein the first structural layer is arranged on a top of the substrate; the single-hole liquid storage cavity and the buffer flow channel are arranged in the first structural layer and are independent of each other; the liquid resistance flow channel is arranged in the first structural layer; two ends of the liquid resistance flow channel are respectively communicated with the single-hole liquid storage cavity and the buffer flow channel; the second structural layer is arranged on a top of the first structural layer and covers a top of the buffer flow channel; the sample flow channel is communicated with the single-hole liquid storage cavity; and the sensing electrode is arranged in the substrate; one end of the sensing electrode is connected to the single-hole liquid storage cavity for detecting a voltage applied to a side of the single-hole liquid storage cavity.

In a second aspect, an embodiment of the present disclosure provides a molecular detection chip, including: a molecular detection array; wherein the molecular detection array includes at least one row of molecular detection units; each row of molecular detection units includes a plurality of molecular detection units as described above; the sample flow channels of the plurality of molecular detection units in each row of molecular detection units are connected to each other as a common sample flow channel; and the buffer flow channels of the plurality of molecular detection units in each row of molecular detection units are connected to each other as a common buffer flow channel.

In a third aspect, embodiments of the present disclosure provide a method for preparing the molecular detection chip, including:
- preparing a substrate, and forming a sensing electrode of each molecular detection unit in a molecular detection chip on the substrate respectively; the sensing electrode is used to detect a voltage applied to a side of the single-hole liquid storage cavity;
- forming a first structural layer on the substrate, and forming a corresponding single-hole liquid storage cavity, liquid resistance flow channel and buffer flow channel for each molecular detection unit in the molecular detection chip in the first structural layer, and the buffer flow channels of a plurality of molecular detection units in each row of molecular detection units being communicated with each other as a common buffer flow channel;
- for a molecular detection array, forming a second structural layer on the first structural layer, sealing the common buffer flow channel and the buffer flow channel of each molecular detection unit, and forming a sample flow channel for each molecular detection unit in the second structural layer, and the sample flow channels of a plurality of molecular detection units in each row of molecular detection units being communicated with each other as a common sample flow channel;
- forming a third structural layer on the second structural layer, and forming sample access holes communicated with two ends of the common sample flow channel and forming buffer access holes communicated with two ends of the common buffer flow channel for the molecular detection array; and
- forming an upper cover on the third structural layer, and forming a first interface and a second interface on the upper cover for the molecular detection array; here, the first interface is located above the sample access hole, and the second interface is located above the buffer access hole.

BRIEF DESCRIPTION OF THE DRAWINGS

The accompanying drawings are used to better understand the present solution, and do not constitute a limitation to the present disclosure.

DETAILED DESCRIPTION OF THE EMBODIMENTS

It should be noted that the following detailed description is exemplary and intended to provide further explanation of the present disclosure. Unless defined otherwise, all technical and scientific terms used herein have the same meaning as commonly understood by one of ordinary skill in the art to which this disclosure belongs.

It should be noted that the terminology used herein is only for describing specific embodiments, and is not intended to limit the exemplary embodiments according to the present disclosure. As used herein, unless the context clearly dictates otherwise, the singular is intended to include the plural, and it should also be understood that when the terms "comprising" and/or "comprising" are used in this specification, they indicate the presence of features, steps, operations, devices, components, and/or combinations of them.

In the case of no conflict, the embodiments in the present disclosure and the features in the embodiments can be combined with each other.

In order to make the technical solutions and advantages of the present disclosure clearer, the present disclosure will be further described in detail below in conjunction with the accompanying drawings and specific embodiments.

A molecular detection unit is proposed in the present disclosure.

Figure 1:
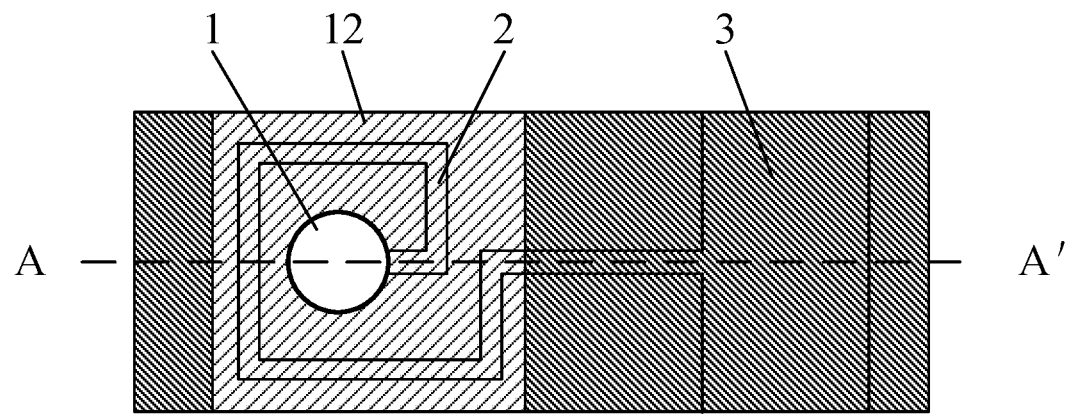
FIG. 1 is a schematic structural diagram of a molecular detection unit in a specific embodiment of the present disclosure.
Figure 2:
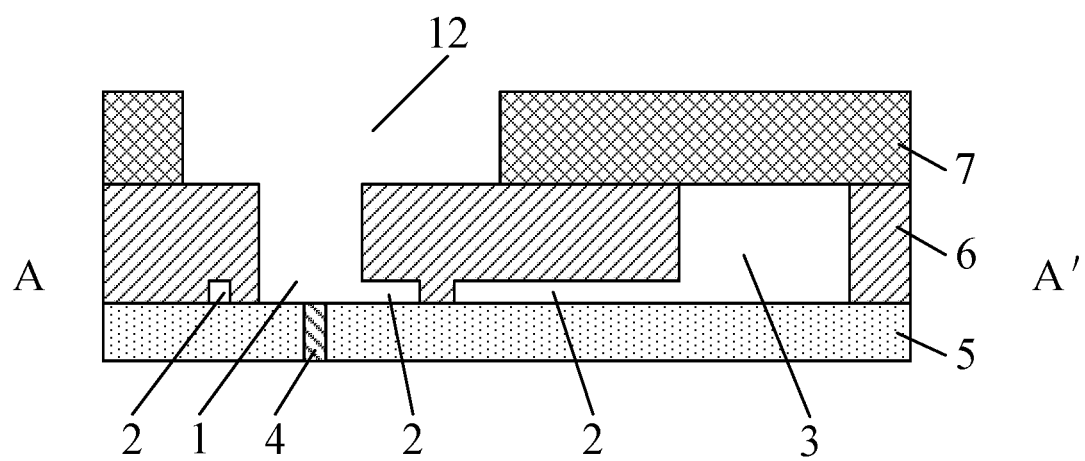
FIG. 2 is a schematic cross-sectional view of AA' in FIG. 1.

As shown in FIGS. 1 and 2, in a specific embodiment of the present disclosure, the molecular detection unit may including: a single-hole liquid storage cavity 1, a liquid resistance flow channel 2, a buffer flow channel 3, a sensing electrode 4, a substrate 5, a first structural layer 6, a second structural layer 7 and a sample flow channel 12; the first structural layer 6 is arranged on a top of the substrate 5; the single-hole liquid storage cavity 1 and the buffer flow channel 3 are arranged in the first structural layer 6 and are independent of each other; the liquid resistance flow channel 2 is arranged in the first structural layer 6; two ends of the liquid resistance flow channel 2 are respectively communicated with the single-hole liquid storage cavity 1 and the buffer flow channel 3; the second structural layer 7 is arranged on a top of the first structural layer 6 and covers a top of the buffer flow channel 3; the sample flow channel 12 is communicated with the single-hole liquid storage cavity 1; and the sensing electrode 4 is arranged in the substrate 5; one end of the sensing electrode 4 is connected to the single-hole liquid storage cavity 1.

In addition, in the technical solution of the present disclosure, according to the needs of actual application scenarios, corresponding membrane layers and nanopores can be further provided in the above-mentioned molecular detection unit.

Figure 3:
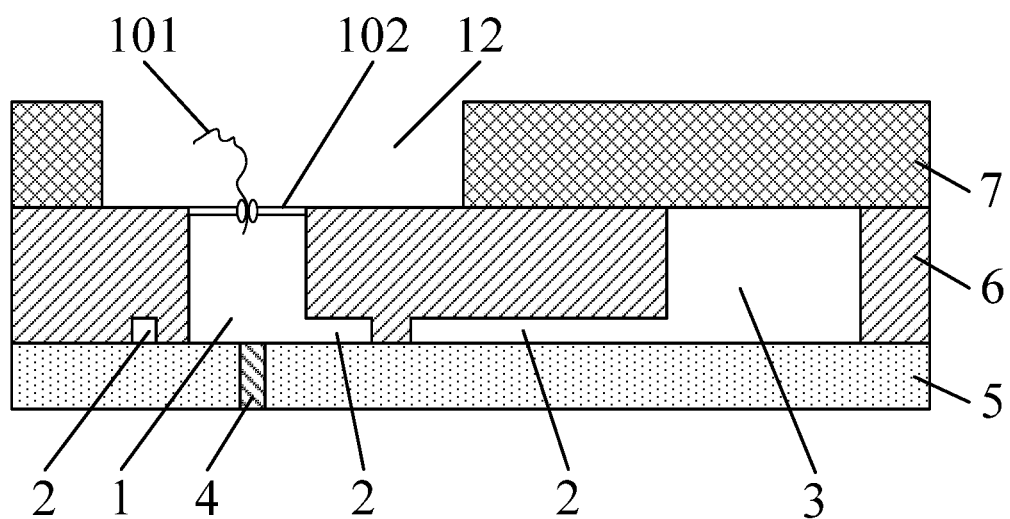
FIG. 3 is a schematic structural diagram of a molecular detection unit with a membrane layer in a specific embodiment of the present disclosure.

For example, as an example, as shown in FIG. 3, in a specific embodiment of the present disclosure, the above-mentioned molecular detection unit may further include: a membrane layer 102; the membrane layer 102 is arranged at the junction of the sample flow channel 12 and the single-hole liquid storage cavity 1; the membrane layer 102 is provided with a nanopore.

In addition, in the technical solution of the present disclosure, different membrane layers can also be formed in the above-mentioned molecular detection unit according to the needs of actual application scenarios.

For example, as an example, in a specific embodiment of the present disclosure, the membrane layer 102 may be a bimolecular layer or a monomolecular layer.

For example, when the material of the membrane layer is phospholipid, the membrane layer 102 is a bimolecular layer; and when the material of the membrane layer is other polymer materials, the membrane layer 102 is a monomolecular layer.

Before using the above-mentioned molecular detection unit, considering storage, transportation and other requirements, the sample flow channel 12 and the buffer flow channel 3 can be injected and filled with buffer (a polar solution containing required electrolytes) respectively. Since the single-hole liquid storage cavity 1 communicates with the buffer flow channel 3 through the liquid resistance flow channel 2, the single-hole liquid storage cavity 1 and the liquid resistance flow channel 2 will also be filled with buffer.

When the above-mentioned molecular detection unit needs to be used, the sample solution can be injected into the sample flow channel 12 to replace the original buffer in the sample flow channel 12.

During this process, the positive or negative pressure provided by an external pump can be used to drive the liquid to flow. For example, when positive pressure is used to drive the sample solution into the sample flow channel 12, the sample solution in the sample solution storage device (such as a liquid storage bottle, etc.) will enter from one end of the sample flow channel 12 under the pressure provided by the external pump, and flow through the sample flow channel 12 and leave the sample flow channel 12 from the other end of the sample flow channel 12, and be collected by a waste liquid collection device (such as a waste liquid bottle, etc.) to prevent contamination.

Driven by pressure, the Reynolds number of the sample solution is low when it moves in the sample flow channel 12, so the sample solution exhibits a laminar flow state, and at this time the sample solution will not pass through the membrane layer 102 and enter the single-hole liquid storage cavity 1. And when there is no pressure to drive, the membrane layer 102 acts as a thin film between the single-hole liquid storage cavity 1 and the sample flow channel 12, which can also prevent mutual diffusion between the sample solution in the sample flow channel 12 and the buffer in the single-hole liquid storage cavity 1.

When the above-mentioned molecular detection unit is in the working state, a voltage can be applied to the side of the sample flow channel 12 (for example, a voltage is applied to the sample solution in the sample flow channel 12, which can be denoted as V3), and a voltage can be applied to the side of the buffer flow channel 3 (for example, a voltage is applied to the buffer in the buffer flow channel 3, which can be denoted as V2). Due to the existence of the liquid resistance flow channel 2, there is a certain difference between the voltage V1 and the voltage V2 finally applied to the side of the single-hole liquid storage cavity 1. When the DNA molecule 101 in the sample solution passes through the nanopore (for example, nanoporin) embedded in the membrane layer 102, the ratio of the resistance value between the membrane layer 102 embedded with the nanopore and the liquid resistance flow channel 2 will change. Therefore, according to the change law of the voltage V1 detected by the sensing electrode 4, the base arrangement of the DNA molecule 101 can be determined.

In the above-mentioned molecular detection unit of the present disclosure, the single-hole liquid storage cavity 1, the liquid resistance flow channel 2, the buffer flow channel 3 and the sample flow channel 12 are all arranged on the same side of the substrate 5, so the liquid resistance flow channel and the buffer flow channel can be constructed on the same surface of the substrate, which can effectively improve the chip production efficiency based on the voltage sequencing method, and further improve the flux of the nanopore sequencing device.

In addition, in the above-mentioned molecular detection unit of the present disclosure, the sample flow channel 12 and the buffer flow channel 3 are isolated from each other, and the sample solution can flow in from one end of the sample flow channel 12, and then flow out from the other end of the sample flow channel 12, and the sample solution will not enter the buffer flow channel 3; similarly, the buffer can flow in from one end of the buffer flow channel 3, and then flow out from the other end of the buffer flow channel 3, and the buffer in the buffer flow channel 3 will not enter the sample flow channel 12.

Since the above two flow channels are separated, different voltages can be applied to different liquids in the two flow channels, thus ensuring the realization of the basic principle of voltage sequencing. In addition, the above separated two flow channels can also greatly reduce cross-contamination and electric leakage between samples, and improve the signal-to-noise ratio of the signal.

Figure 4:
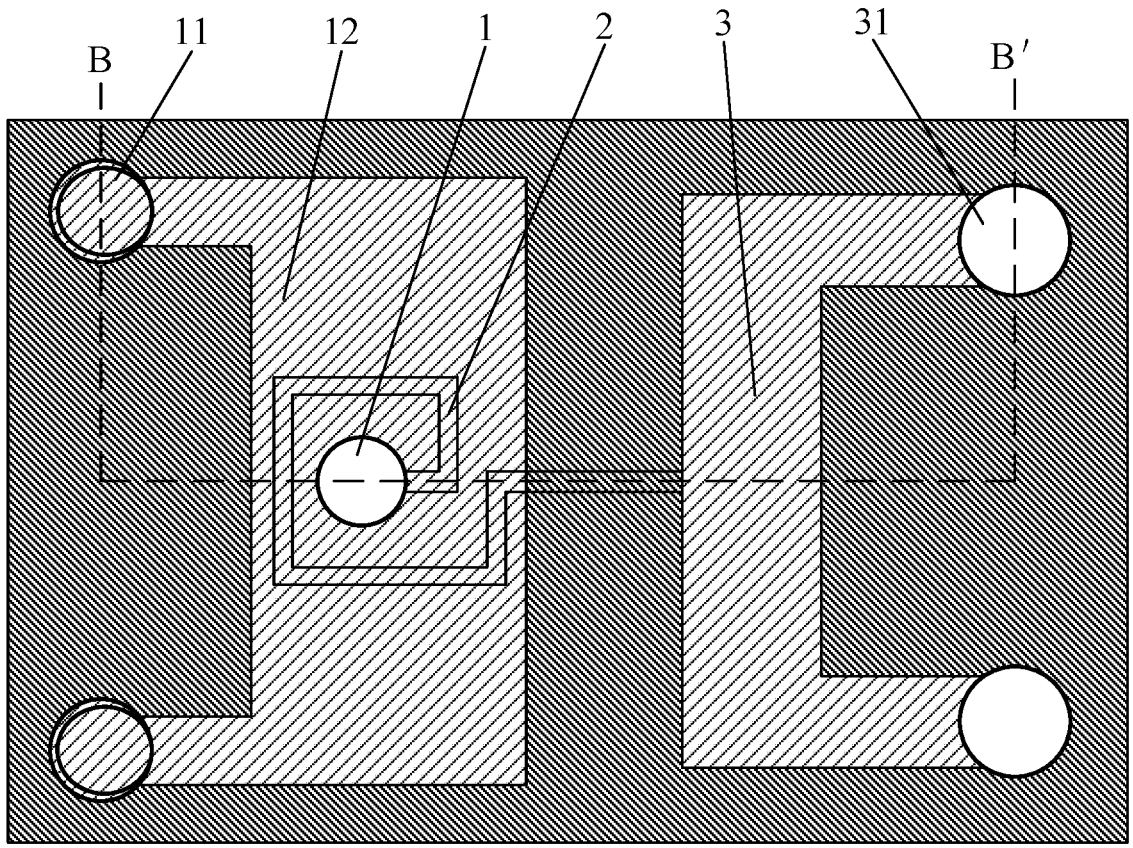
FIG. 4 is a schematic structural diagram of a molecular detection unit in another specific embodiment of the present disclosure.
Figure 5:
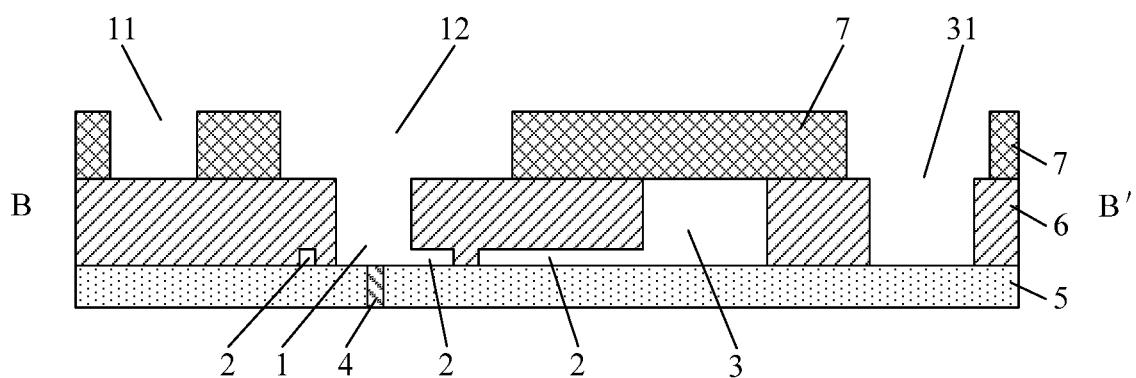
FIG. 5 is a schematic cross-sectional view of BB' in FIG. 4.

In addition, as an example, as shown in FIG. 4 and FIG. 5, in a specific embodiment of the present disclosure, the above-mentioned molecular detection unit may further include: two sample access holes 11 and two buffer access holes 31; the two sample access holes 11 are respectively communicated with two ends of the sample flow channel 12; the two buffer access holes 31 are respectively communicated with two ends of the buffer flow channel 3.

For example, as shown in FIG. 4 and FIG. 5, the above-mentioned sample access hole 11 can penetrate through the second structural layer 7 to communicate with the sample flow channel 12 in the second structural layer 7; while the buffer access hole 31 can communicate with the buffer flow channel 3 in the first structural layer 6 after penetrating through the second structural layer 7 and the first structural layer 6.

In the above-mentioned molecular detection unit, the sample flow channel 12 and the two sample access holes 11 can form a sample microchannel system, while the buffer flow channel 3 and the two buffer access holes 31 can form a buffer microchannel system. The liquids of the two microchannel systems enter from one access hole of the system, and then flow out from the other access hole, and are isolated from each other. For example, the sample solution will only enter the sample flow channel 12 from one sample access hole 11, and then flow out of the sample flow channel 12 from the other sample access hole 11; during this process, the sample solution will not enter the buffer microchannel system. Equally, buffer can enter buffer flow channel 3 from one buffer access hole 31, and then flow out of the buffer flow channel 3 from the other buffer access hole 31; during this process, the buffer in the buffer microchannel system will not enter the sample microchannel system.

Since the above two microchannel systems are separated, different voltages can be applied to different liquids in the two microchannel systems, thus ensuring the realization of the basic principle of voltage sequencing. In addition, the above-mentioned two separated microchannel systems can also greatly reduce cross-contamination and electric leakage between samples, and improve the signal-to-noise ratio of the signal.

In addition, as an example, in a specific embodiment of the present disclosure, the above-mentioned molecular detection unit may further include: a third structural layer 8; the third structural layer 8 is arranged on top of the second structural layer 7.

Figure 6:
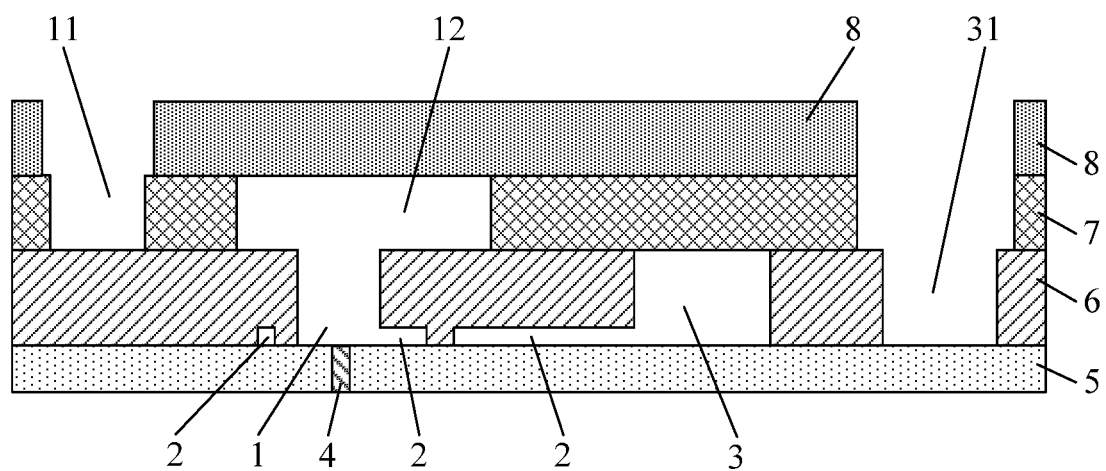
FIG. 6 is a schematic cross-sectional view of a molecular detection unit in another specific embodiment of the present disclosure.

In addition, as an example, as shown in FIG. 6, in a specific embodiment of the present disclosure, the above-mentioned third structural layer 8 may cover the top of the sample flow channel 12.

Through the above-mentioned third structural layer 8, the sample flow channel 12 can be further sealed.

In addition, as an example, in a specific embodiment of the present disclosure, the top of the sample access hole 11 and the top of the buffer access hole 31 can also be formed in the third structural layer 8, thereby forming a complete sample access hole 11 and buffer access hole 31.

Figure 7:
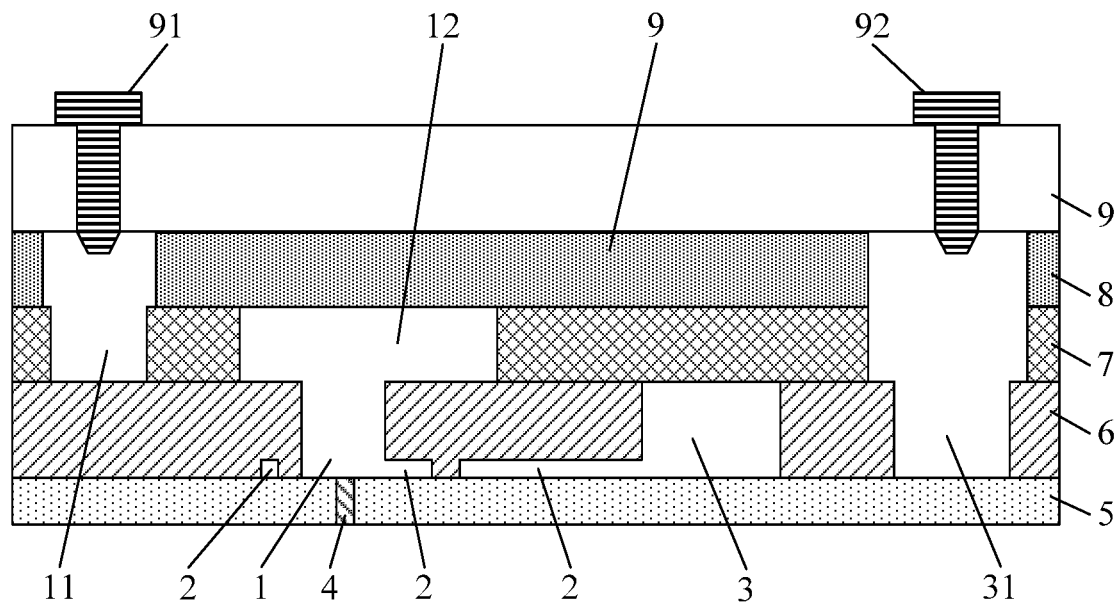
FIG. 7 is a schematic cross-sectional view of a molecular detection unit in another embodiment of the present disclosure.

In addition, as an example, as shown in FIG. 7, in a specific embodiment of the present disclosure, the above-mentioned molecular detection unit may further include: an upper cover 9, a first interface 91 and a second interface 92; the upper cover 9 is arranged on the third structural layer 8, and covers the top of the sample access hole 11 and the buffer access hole 31; the top of the sample access hole 11 is provided with the first interface 91 penetrating through the upper cover 9; the top of the buffer access hole 31 is provided with the second interface 92 penetrating through the upper cover 9.

In the technical solution of the present disclosure, the above-mentioned upper cover 9 may be bonded to the third structural layer 8 in a certain way to form a microfluidic chip. In addition, the above-mentioned first interface 91 and second interface 92 can also be formed on the upper cover 9, that is, a first interface 91 is arranged on the top of each sample access hole 11, and a second interface 92 is arranged on the top of each buffer access hole 31, so as to communicate with the sample access hole 11 through the first interface 91 and communicate with the buffer access hole 31 through the second interface 92.

In addition, as an example, in a specific embodiment of the present disclosure, the first interface 91 may also be provided with a first driving electrode, and the second interface 92 may also be provided with a second driving electrode.

At this time, the above-mentioned first interface 91 and second interface 92 can be a structure that allows liquid to enter and exit and driving electrodes to be connected, so that the corresponding liquid can be injected into the sample access hole 11 through the first interface 91 or the corresponding liquid can flow out from the sample access hole 11 through the first interface 91, and a corresponding voltage can be applied to the liquid in the sample flow channel 12 through the first driving electrode in the first interface 91. Similarly, the corresponding liquid can be injected into the buffer access hole 31 through the above-mentioned second interface 92 or the corresponding liquid can flow out from the buffer access hole 31, and a corresponding voltage can be applied to the liquid in the buffer flow channel 3 through the second driving electrode in the second interface 92.

Figure 8:
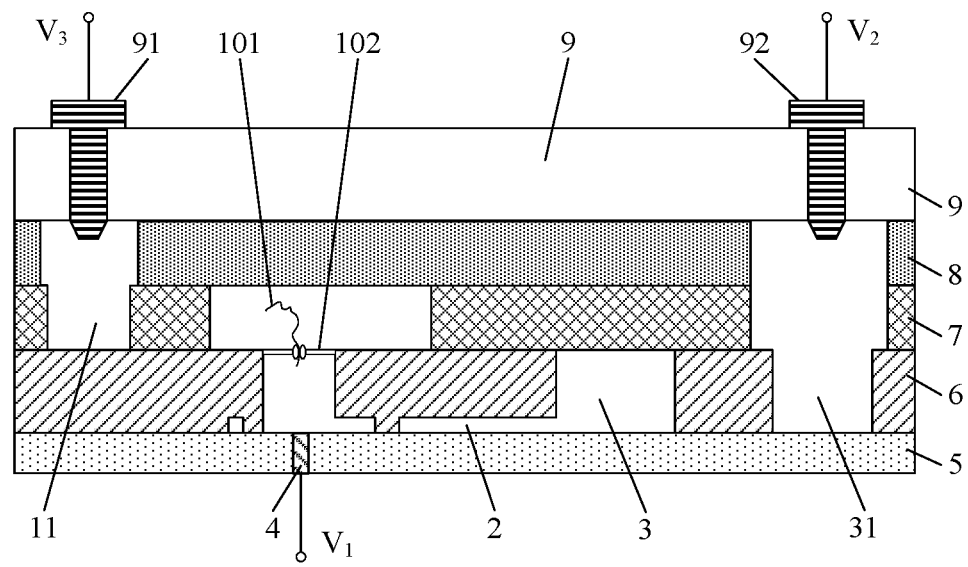
FIG. 8 is a first schematic diagram of the working principle of the molecular detection unit in a specific embodiment of the present disclosure.

For example, in the technical solution of the present disclosure, a membrane layer 102 can be formed at the junction of the single-hole liquid storage cavity 1 and the sample flow channel 12, and nanopores can be formed on the membrane layer 102, as shown in FIG. 8.

When it is necessary to use the above-mentioned molecular detection device to sequence DNA molecules, the sample solution can be injected into the sample flow channel 12 from a sample access hole 11 through the first interface 91 to replace the original buffer in the sample flow channel 12; then, a voltage V3 can be applied to the side of the membrane layer 102 located in the sample flow channel 12 through the first interface 91, and a voltage V2 can be applied to the side of the membrane layer 102 located in the buffer flow channel 3 through the second interface 92 (as shown in FIG. 8); due to the existence of the liquid resistance flow channel 2, the voltage V1 finally applied to the side of the single-hole liquid storage cavity 1 will have a certain difference from the voltage V2. When the DNA molecule 101 in the sample solution passes through the nanopore (for example, nanoporin) embedded in the membrane layer 102, the ratio of the resistance value between the membrane layer 102 embedded with the nanopore and the liquid resistance flow channel 2 will change. Therefore, according to the change rule of the voltage V1 detected by the sensing electrode 4, the base arrangement of the DNA molecule 101 can be calculated to realize the sequencing of the DNA molecule 101.

Figure 9:
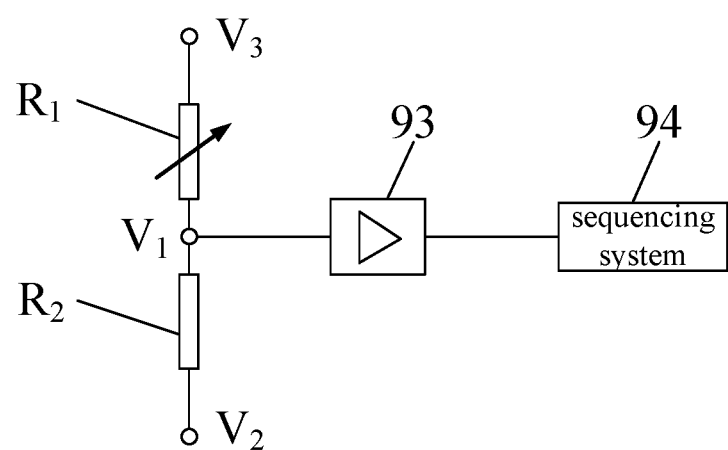
FIG. 9 is a second schematic diagram of the working principle of the molecular detection unit in a specific embodiment of the present disclosure.

For example, as an example, in another specific embodiment of the present disclosure, the above-mentioned resistance between the voltages V2 and V3 is mainly composed of the resistance R1 of the membrane layer 102 embedded with nanopores and the resistance R2 of the liquid resistance flow channel 2, the voltage V1 will be collected and amplified by an amplification circuit 93, and transmitted and recorded into the electrical signal database of the sequencing system 94 (for example, a computer, etc.), as shown in FIG. 9. During the sequencing process, DNA molecules will pass through the nanopore, and there are differences in the combination of DNA bases passing through the nanopore at different times, resulting in the overall resistance R1 of the membrane layer 102 embedded with the nanopore changing with time, that is, the resistance R1 can be regarded as a variable resistor. Therefore, the total resistance of the membrane layer 102 embedded with the nanopore and the base combination currently passing through the nanopore can be determined by the voltage V1 at a given moment, and then, using deep learning algorithms, the DNA molecular base sequence passing through the porin can be calculated.

In addition, in the technical solution of the present disclosure, the driving electrodes in the above-mentioned molecular detection unit can also be flexibly arranged according to the needs of actual application scenarios.

For example, as an example, in another specific embodiment of the present disclosure, the above-mentioned molecular detection unit may further include: a first driving electrode 41 and a second driving electrode 42; the first driving electrode 41 is arranged in the first interface 91, and one end of the first driving electrode 41 is connected to a sample access hole 11, so that a corresponding voltage can be applied to the liquid in the sample flow channel 12 through the first driving electrode 41; the second driving electrode 42 is arranged in the second interface 92, and one end of the second driving electrode 42 is connected to a buffer access hole 31, so that a corresponding voltage can be applied to the liquid in the buffer flow channel 3 through t the second driving electrode 42.

Figure 10:
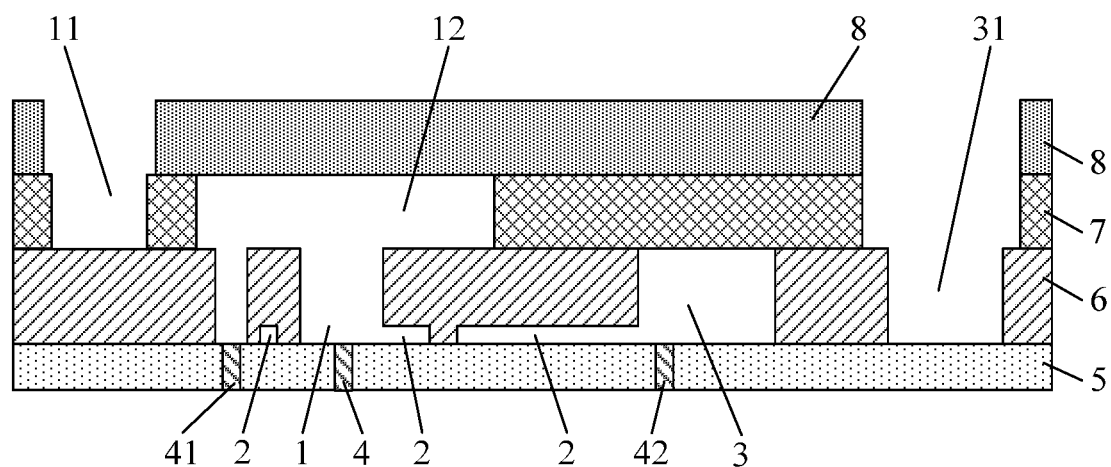
FIG. 10 is a schematic cross-sectional view of a molecular detection unit in another embodiment of the present disclosure.

For another example, as shown in FIG. 10, in another specific embodiment of the present disclosure, the above-mentioned molecular detection unit may further include: a first driving electrode 41 and a second driving electrode 42; the first driving electrode 41 is arranged at the bottom of the sample flow channel 12, and one end of the first driving electrode 41 is connected to the sample flow channel 12; the second driving electrode 42 is disposed at the bottom of the buffer flow channel 3, and one end of the second driving electrode 42 is connected to the buffer flow channel 3.

In the above specific embodiments, the first driving electrode 41 and the second driving electrode 42 may be respectively arranged at the bottom of the sample flow channel 12 and the buffer flow channel 3. Therefore, the first driving electrode 41 can be directly connected to the sample flow channel 12, so that a corresponding voltage can be applied to the liquid in the sample flow channel 12 through the first driving electrode 41; the second driving electrode 42 can be directly connected to the buffer flow channel 3, so that a corresponding voltage can be applied to the liquid in the buffer flow channel 3 through the second driving electrode 42.

In addition, as an example, as shown in FIG. 10, in a specific embodiment of the present disclosure, the first driving electrodes 41 and the second driving electrodes 42 may be arranged in the substrate 5. One end of the first driving electrode 41 can be exposed to the sample flow channel 12 in the second structural layer 7 by the first structural layer 6 (for example, through holes that can expose the first driving electrode 41 can be respectively provided in the substrate 5), so that one end of the first driving electrode 41 can be connected to the sample flow channel 12, and one end of the second driving electrode 42 can be exposed to the buffer flow channel 3 in the first structural layer 6, so that one end of the second driving electrode 42 can be connected to the buffer flow channel 3. Certainly, the first driving electrodes 41 and the second driving electrodes 42 may also be arranged at other suitable positions, which will not be listed here.

Figure 11:
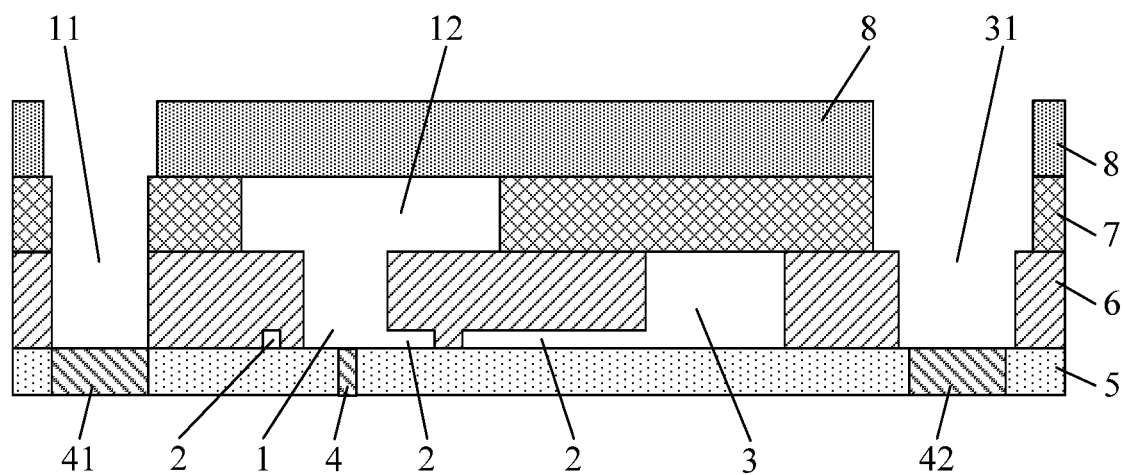
FIG. 11 is a schematic cross-sectional view of a molecular detection unit in another embodiment of the present disclosure.
Figure 12:
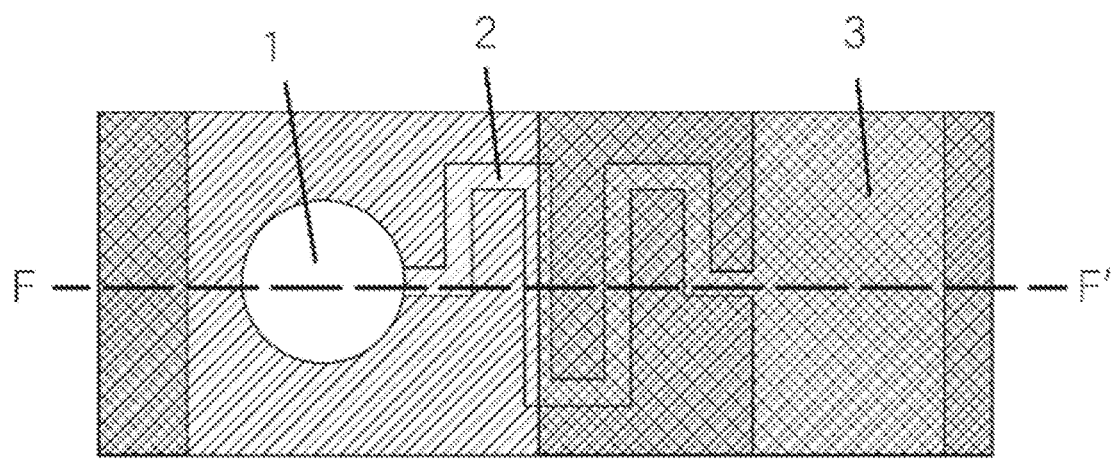
FIG. 12 is a schematic diagram of the shape of a liquid resistance flow channel in a specific embodiment of the present disclosure.
Figure 13:
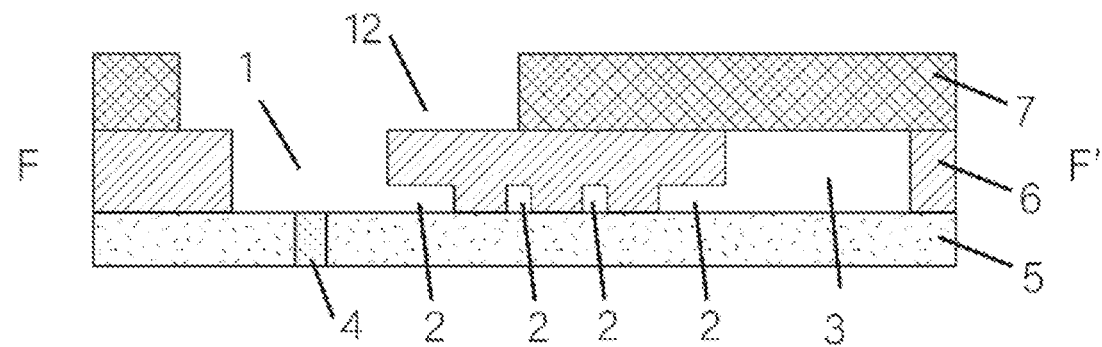
FIG. 13 is a schematic cross-sectional view of FF' in FIG. 12.

For another example, as shown in FIG. 11, in another specific embodiment of the present disclosure, the above-mentioned molecular detection unit may further include: a first driving electrode 41 and a second driving electrode 42; the first driving electrode 41 is arranged at the bottom of the sample access hole 11, and one end of the first driving electrode 41 is connected to the sample access hole 11; the second driving electrode 42 is arranged at the bottom of the buffer access hole 31, and one end of the second driving electrode 42 is connected to the buffer access hole 31.

In the specific embodiment above, the first driving electrode 41 and the second driving electrode 42 may be respectively arranged at the bottom of the sample access hole 11 and the buffer access hole 31. Therefore, the first driving electrode 41 can be connected to the sample access hole 11, so that a corresponding voltage can be applied to the liquid in the sample flow channel 12 through the first driving electrode 41; the second driving electrode 42 can be connected to the buffer access hole 31, so that a corresponding voltage can be applied to the liquid in the buffer flow channel 3 through the second driving electrode 42.

In addition, as an example, as shown in FIG. 11, in a specific embodiment of the present disclosure, the first driving electrodes 41 and the second driving electrodes 42 may also be arranged in the substrate 5. One end of the first driving electrode 41 and the second driving electrode 42 can be exposed by the first structural layer 6 (for example, through holes that can expose the first driving electrode 41 and the second driving electrode 42 can be respectively provided in the substrate 5), so that one end of the first driving electrode 41 can be connected to the sample access hole 11, and one end of the second driving electrode 42 can be connected to the buffer access hole 31. Certainly, the first driving electrodes 41 and the second driving electrodes 42 may also be arranged at other suitable positions, which will not be listed here.

At this time, both the sample access hole 11 and the buffer access hole 31 can penetrate through the first structural layer 6, the second structural layer 7 and the third structural layer 8, so that the first driving electrode 41 can be communicated with the liquid in the sample flow channel 12, and the second driving electrode 42 can be communicated with the liquid in the buffer flow channel 3.

In addition, in the technical solution of the present disclosure, the positional relationship between the sample flow channel 12 and the single-hole liquid storage cavity 1 can also be pre-designed according to actual application requirements.

For example, as an example, as shown in FIG. 2, FIG. 3, and FIG. 5-8, in a specific embodiment of the present disclosure, the sample flow channel 12 can be arranged in the second structural layer 7 and located at the top of the single-hole liquid storage cavity 1. At this time, the sample flow channel 12 is arranged in the second structural layer 7, while the single-hole liquid storage cavity 1 is arranged in the first structural layer 6, and the two are respectively arranged in different layers.

For another example, as an example, as shown in FIG. 49-52, in a specific embodiment of the present disclosure, the sample flow channel 12 can be arranged in the first structural layer 6 and located on one side of the single-hole liquid storage cavity 1 (for example, it can be located on the outside of the single-hole liquid storage cavity 1, that is, the side of the single-hole liquid storage cavity 1 away from the buffer flow channel 3); the second structural layer 7 covers the top of the sample flow channel 12 and the single-hole liquid storage cavity 1. At this time, the sample flow channel 12 and the single-hole liquid storage cavity 1 are arranged in the same structural layer.

In addition, in the technical solution of the present disclosure, the shape of the liquid resistance flow channel 2 can be set according to the needs of the actual application scenarios.

For example, as shown in FIG. 1, FIG. 4, FIG. 12 and FIG. 13, in a specific embodiment of the present disclosure, the shape of the liquid resistance flow channel 2 cab be a single-layer folded line type.

In this embodiment, the liquid resistance flow channel 2 can be a single-layer structure, and the entire liquid resistance flow channel 2 is in the shape of a folded line.

For another example, as an example, in a specific embodiment of the present disclosure, the shape of the liquid resistance flow channel 2 can be a single-layer linear type.

In this embodiment, the liquid resistance flow channel 2 can be a single-layer structure, and the entire liquid resistance flow channel 2 is in the shape of a straight line.

Figure 14:
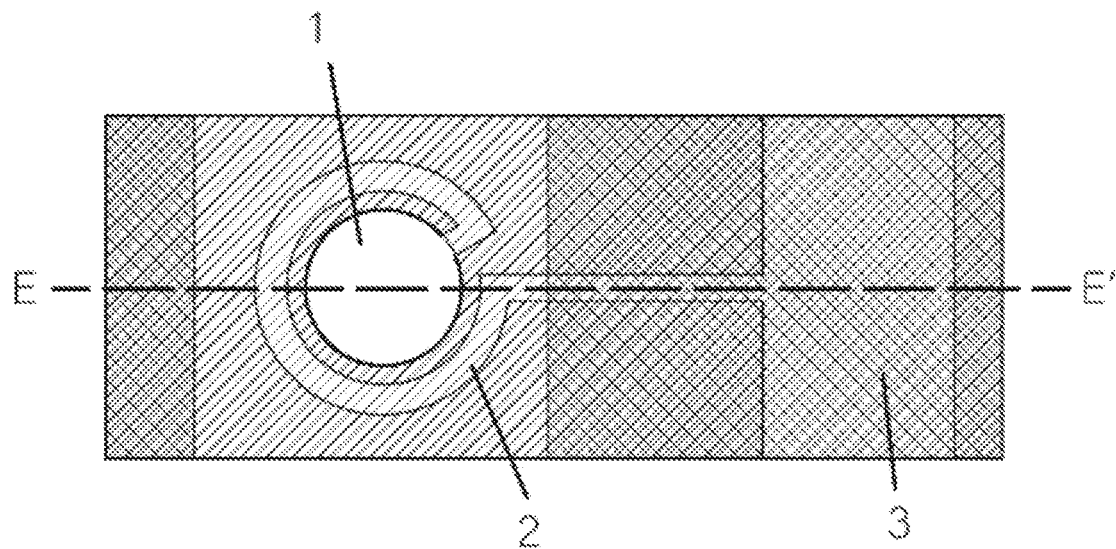
FIG. 14 is a schematic diagram of the shape of a liquid resistance flow channel in another specific embodiment of the present disclosure.
Figure 15:
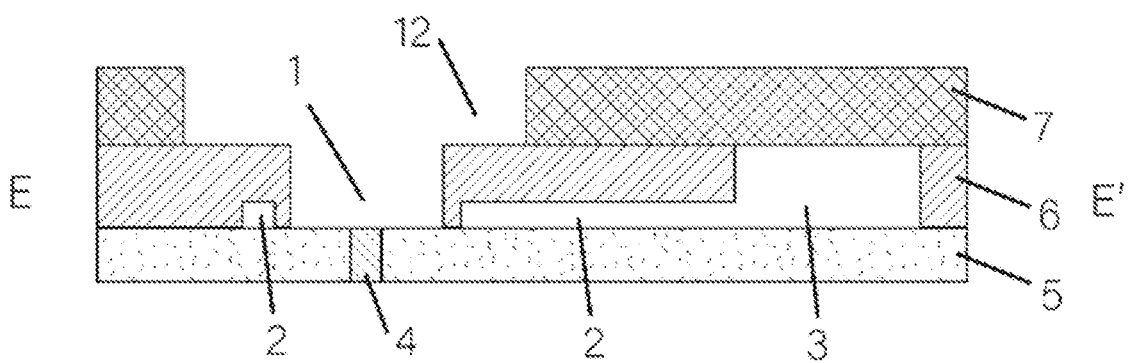
FIG. 15 is a schematic cross-sectional view of EE' in FIG. 14.

For another example, as shown in FIG. 14 and FIG. 15, in another specific embodiment of the present disclosure, the shape of the liquid resistance flow channel 2 can be a single-layer arc type.

In this embodiment, the liquid resistance flow channel 2 can be a single-layer structure, and a part of the liquid resistance flow channel 2 (for example, the part located below the sample flow channel 12) is in the shape of an arc (for example, surrounding the single-hole liquid storage cavity 1), while the other part (for example, the part located between the single-hole liquid storage cavity 1 and the buffer flow channel 3) is in the shape of a straight line.

Figure 16:
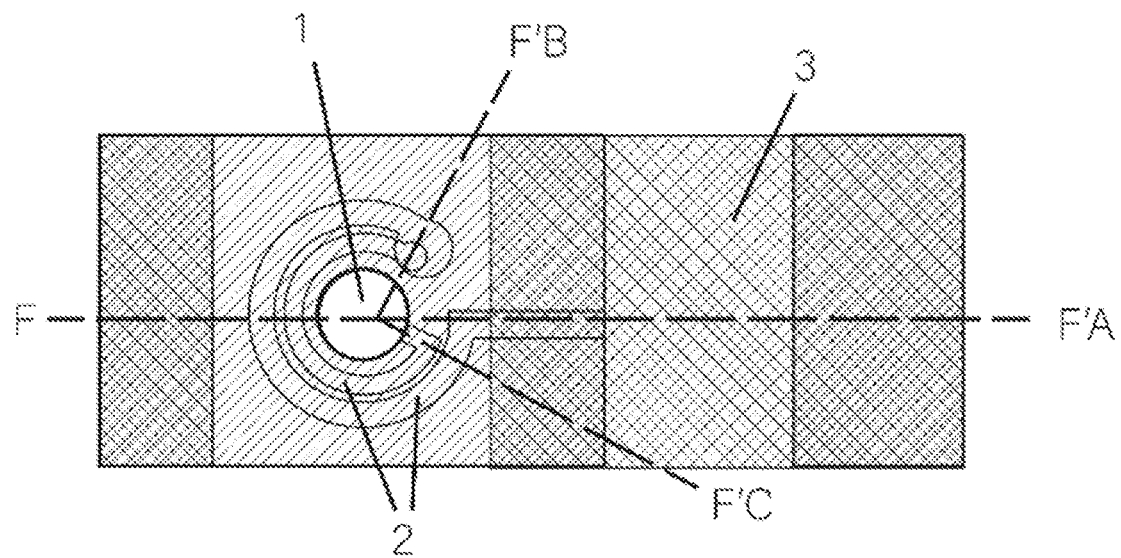
FIG. 16 is a schematic diagram of the shape of a liquid resistance flow channel in another specific embodiment of the present disclosure.
Figure 17:
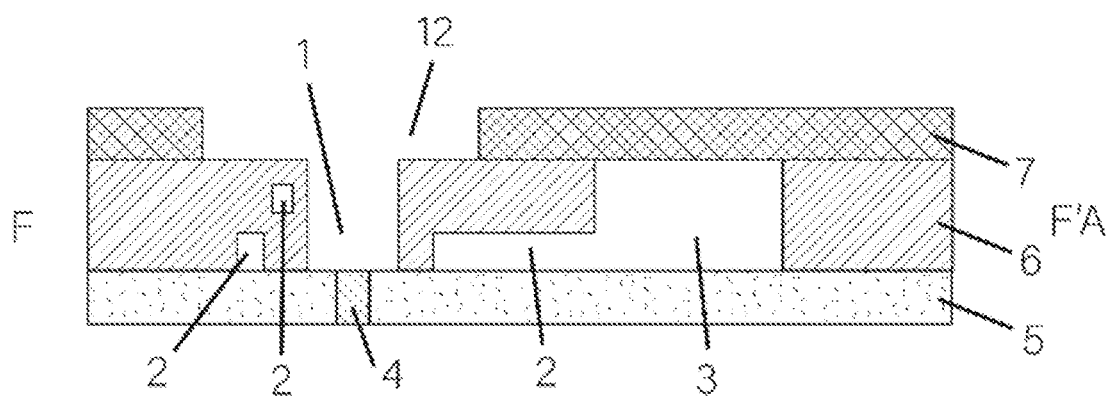
FIG. 17 is a schematic cross-sectional view of FF'A in FIG. 16.
Figure 18:
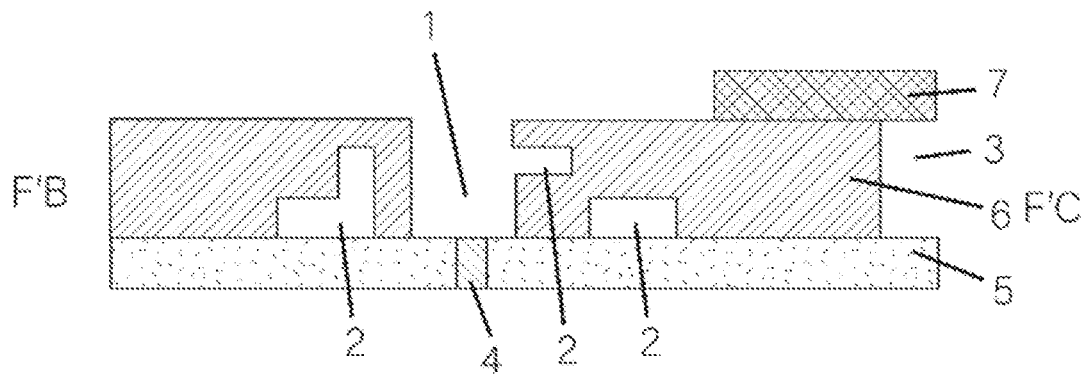
FIG. 18 is a schematic cross-sectional view of F'BF'C in FIG. 16.

For another example, as an example, as shown in FIG. 16-18, in another specific embodiment of the present disclosure, the shape of the liquid resistance flow channel 2 can be a multi-layer arc type.

In this embodiment, the liquid resistance flow channel 2 can be a multi-layer structure, and a part of the liquid resistance flow channel 2 (for example, the part located below the sample flow channel 12) is in the shape of a multi-layer arc (for example, the arcs surrounding the upper and lower layers of the single-hole liquid storage cavity 1), while the other part (for example, the part between the single-hole liquid storage cavity 1 and the buffer flow channel 3) is in the shape of a single-layer straight line.

In addition, in the technical solution of the present disclosure, a molecular detection chip is also proposed.

For example, as an example, in another specific embodiment of the present disclosure, the molecular detection chip includes: a molecular detection array; the molecular detection array includes at least one row of molecular detection units; each row of molecular detection units includes a plurality of molecular detection units; the molecular detection unit can be the molecular detection unit in any one of the above embodiments; the sample flow channels of the plurality of molecular detection units in each row of molecular detection units can be connected to each other as a common sample flow channel; the buffer flow channels of the plurality of molecular detection units in each row of molecular detection units can be connected to each other as a common buffer flow channel.

In the molecular detection chip, a molecular detection array can be arranged, and one or more rows of molecular detection units are arranged in the molecular detection array, and each row of molecular detection units includes a plurality of molecular detection units. In each row of molecular detection units, the sample flow channels of each molecular detection unit can communicate with each other according to their respective arrangement sequences to form a common sample flow channel, and the buffer flow channels of each molecular detection unit in each row of molecular detection units can also communicate with each other according to their respective arrangement sequences to form a common buffer flow channel. Therefore, each molecular detection unit in each row of molecular detection units can share the above-mentioned common sample flow channel, and share the above-mentioned common buffer flow channel. Therefore, the required liquid (for example, buffer and/or sample solution) can be injected into each molecular detection unit through the above-mentioned common sample flow channel, or the required liquid (for example, buffer) can be injected into each molecular detection unit through the above-mentioned common buffer flow channel.

In addition, as an example, in a specific embodiment of the present disclosure, the molecular detection chip may further includes: two sample access holes and two buffer access holes; two ends of the common sample flow channel are respectively communicated with two sample access holes; two ends of the common buffer flow channel are respectively communicated with two buffer access holes.

That is to say, when each molecular detection unit in the molecular detection chip shares a common sample flow channel and a common buffer flow channel, only two sample access holes and two buffer access holes can be arranged in the entire molecular detection chip, and the two ends of the shared common sample flow channel are respectively communicated with two sample access holes; and the two ends of the shared common buffer flow channel are respectively communicated with two buffer access holes. Therefore, it is equivalent to that all the molecular detection units in the molecular detection array share two sample access holes and two buffer access holes. When the above-mentioned molecular detection array needs to be used, the buffer or sample solution can be respectively injected into the sample flow channel of each molecular detection unit from one sample access hole, and flow out of the sample flow channel from another sample access hole; the buffer can be respectively injected into the buffer flow channel of each molecular detection unit from one buffer access hole, and flow out of the buffer flow channel from another buffer access hole.

In addition, in the technical solution of the present disclosure, a row of molecular detection units can be provided in the molecular detection array, or multiple rows of molecular detection units can be provided in the molecular detection array according to the needs of actual application scenarios. In addition, the number of common sample flow channels and/or common buffer flow channels in the molecular detection array can also be preset according to the needs of actual application scenarios.

For example, as an example, in a specific embodiment of the present disclosure, when the molecular detection array includes one or more rows of molecular detection units, the number of common sample flow channels in the molecular detection array can be equal to the number of rows of molecular detection units in the molecular detection array.

For another example, as an example, in another specific embodiment of the present disclosure, when the molecular detection array includes multiple rows of molecular detection units, the number of common sample flow channels in the molecular detection array can be made smaller than the number of rows of molecular detection units in the molecular detection array.

For another example, as an example, in another specific embodiment of the present disclosure, when the molecular detection array includes one or more rows of molecular detection units, the number of common buffer flow channels in the molecular detection array can be equal to the number of rows of molecular detection units in the molecular detection array.

For another example, as an example, in another specific embodiment of the present disclosure, when the molecular detection array includes multiple rows of molecular detection units, the number of common buffer flow channels in the molecular detection array can be made smaller than the number of rows of molecular detection units in the molecular detection array.

In the technical solution of the present disclosure, the above-mentioned specific embodiments may be combined correspondingly according to the requirements of actual application scenarios, so that various specific implementation manners may be obtained. The combination of different specific embodiments in the present disclosure will be described in detail below by taking several specific implementation manners as examples.

Figure 19:
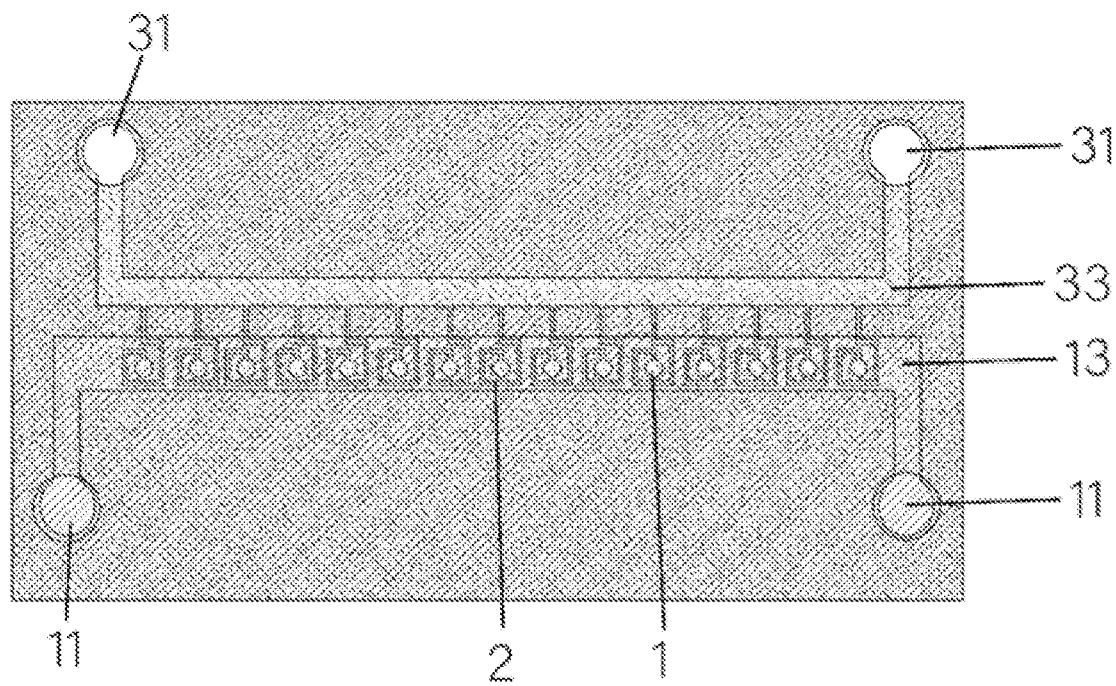
FIG. 19 is a schematic structural diagram of a molecular detection array in a specific embodiment of the present disclosure.

For example, as shown in FIG. 19, in a specific embodiment of the present disclosure, only one row of molecular detection units, one common sample flow channel and one common buffer flow channel may be provided in the molecular detection array. Therefore, the number of common sample flow channels and the number of common buffer flow channels in the molecular detection array are equal to the number of rows of molecular detection units in the molecular detection array, and multiple molecular detection units in a row of molecular detection units share a common sample flow channel 13 and a common buffer flow channel 33.

In this specific embodiment, a plurality of molecular detection units in the molecular detection array are arranged in a row, and a row of molecular detection units includes a plurality of molecular detection units, and the sample flow channels of each molecular detection unit are communicated with each other as a common sample flow channel 13 according to their respective arrangement sequences, and the buffer flow channels of each molecular detection unit are communicated with each other as a common buffer flow channel 33 according to their respective arrangement sequences.

Since the molecular detection array has only one row of molecular detection units, only one common sample flow channel 13 and one common buffer flow channel 33 can be arranged in the molecular detection array. All the molecular detection units in the molecular detection array share the same common sample flow channel 13 and the same common buffer flow channel 33, and share two sample access holes 11 and two buffer access holes 31, and two ends of the common sample flow channel 13 communicate with the two sample access holes 11 respectively, and two ends of the common buffer flow channel 33 communicate with the two buffer access holes 31 respectively.

Figure 20:
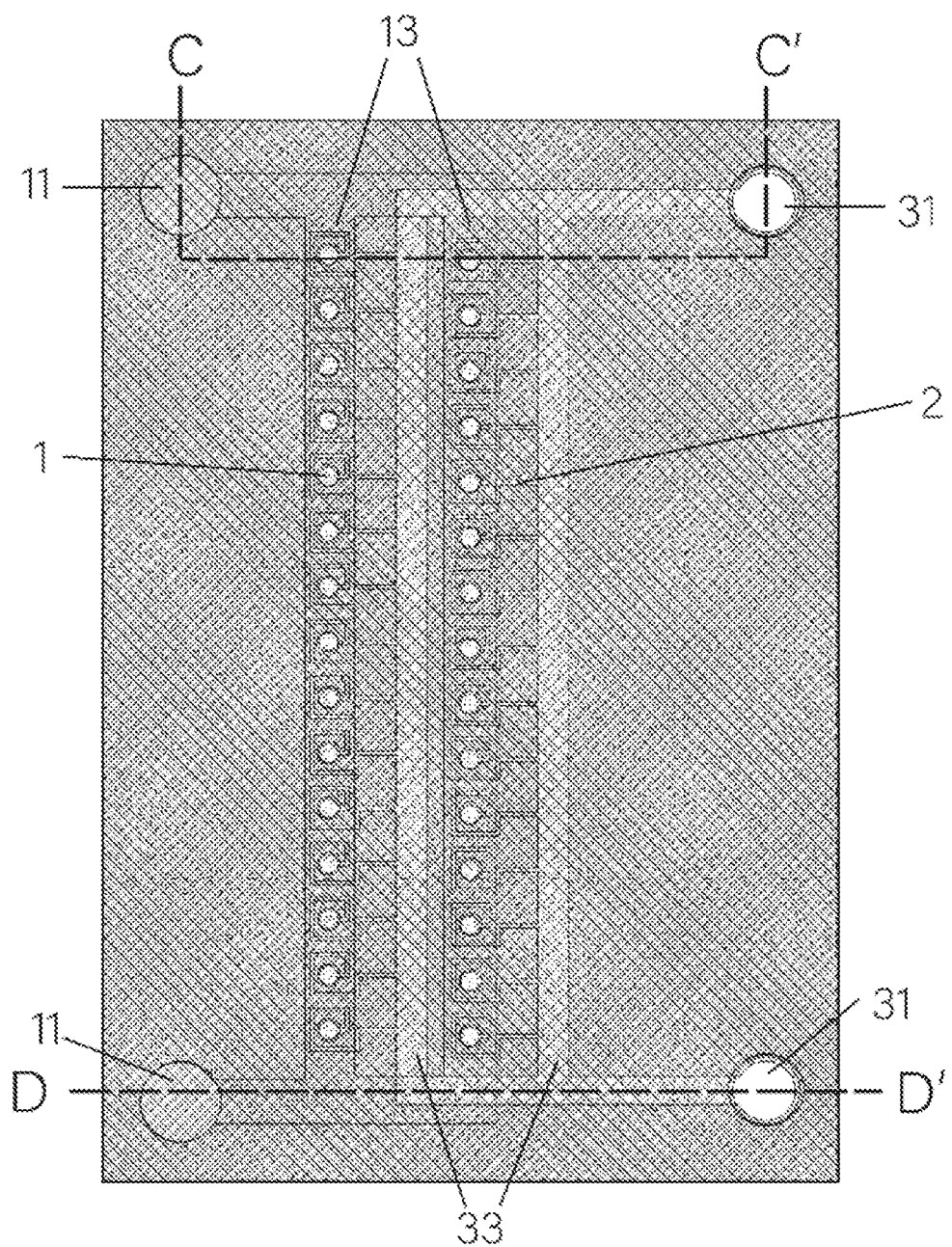
FIG. 20 is a schematic structural diagram of a molecular detection array in another specific embodiment of the present disclosure.

For another example, as shown in FIG. 20-23, in another specific embodiment of the present disclosure, multiple rows of molecular detection units (only two rows of molecular detection units are shown in FIG. 20), multiple common sample flow channels and multiple common buffer flow channels can be arranged in the molecular detection array, and the number of common sample flow channels and common buffer flow channels in the molecular detection array are equal to the number of rows of molecular detection units in the molecular detection array, and each molecular detection unit in the same row shares a common sample flow channel 13 and a common buffer flow channel 33.

In another specific embodiment of the present disclosure, it is assumed that n (n≥2) rows of molecular detection units are arranged in a molecular detection array (for example, only n=2 is shown in FIG. 20, that is, the case of two rows of molecular detection units), and the sample flow channels of each molecular detection unit in each row are communicated with each other as a common sample flow channel 13 according to their respective arrangement sequences, and the buffer flow channels of each molecular detection unit in each row are communicated with each other as a common buffer flow channel 33 according to their respective arrangement sequences, then n common sample flow channels 13 and n common buffer flow channels 33 can be arranged in the molecular detection array, and each row of molecular detection units uses corresponding common sample flow channel 13 and common buffer flow channel 33. Then common sample flow channels 13 share two sample access holes 11, and the n common buffer flow channels 33 share two buffer access holes 31, and two ends of each common sample flow channel 13 are communicate with the two sample access holes 11 respectively, and two ends of the common buffer flow channel 33 are communicate with the two buffer access holes 31 respectively, so n groups of mutually independent flow channel systems are still formed.

Figure 24:
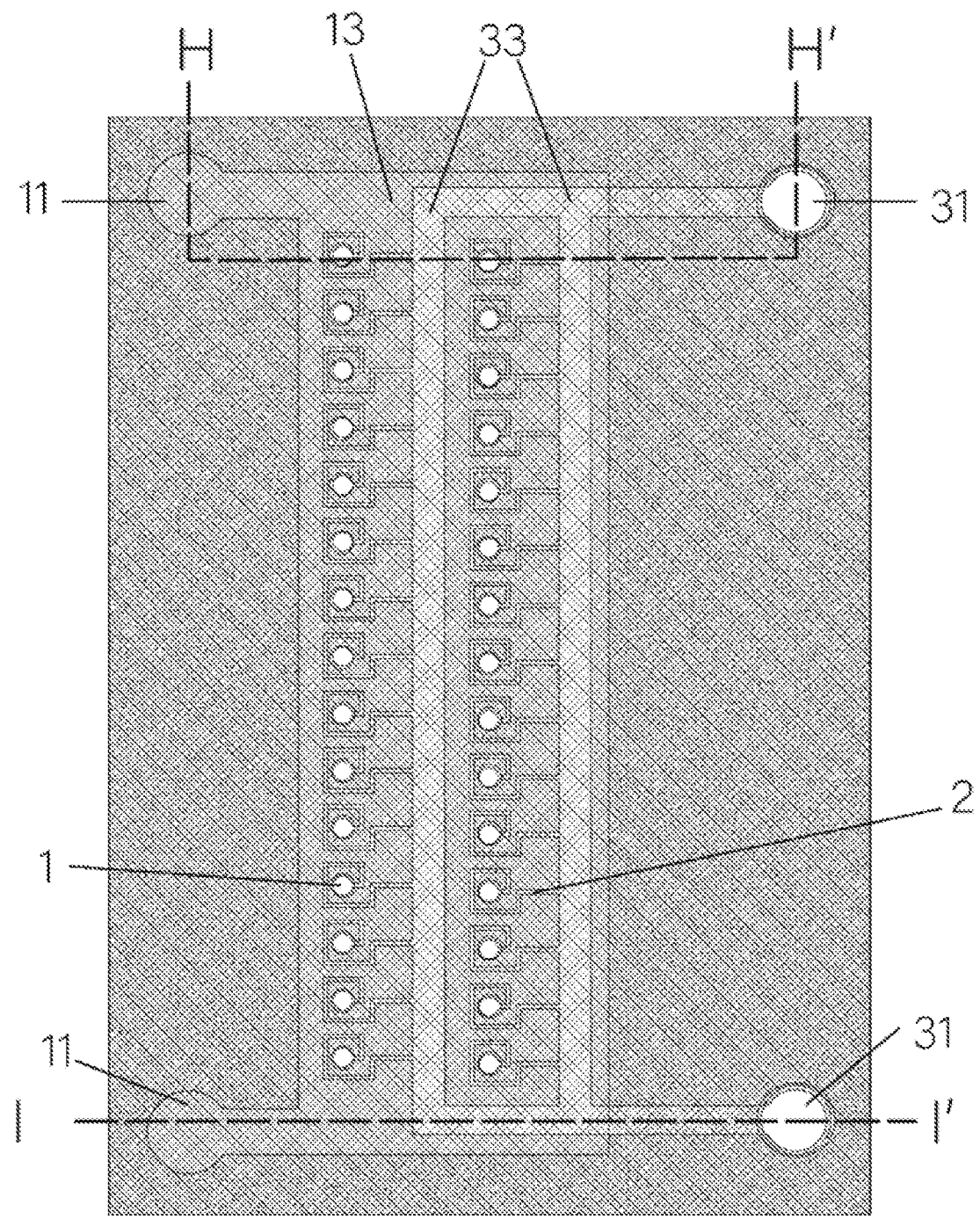
FIG. 24 is a schematic structural diagram of a molecular detection array in another specific embodiment of the present disclosure.
Figure 25:
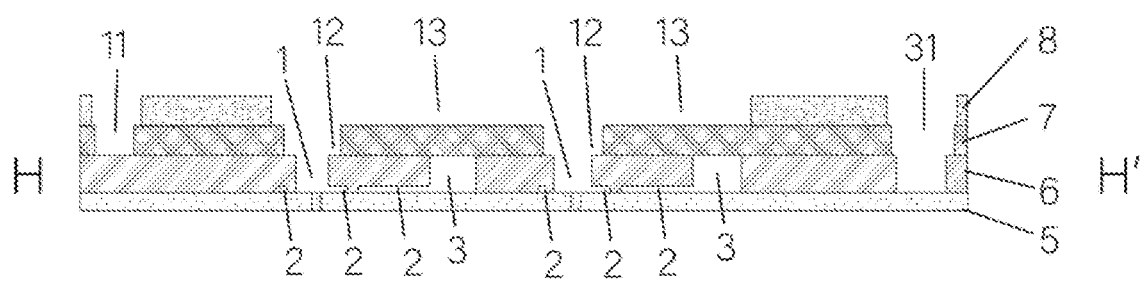
FIG. 25 is a schematic cross-sectional view of in FIG. 24.
Figure 26:
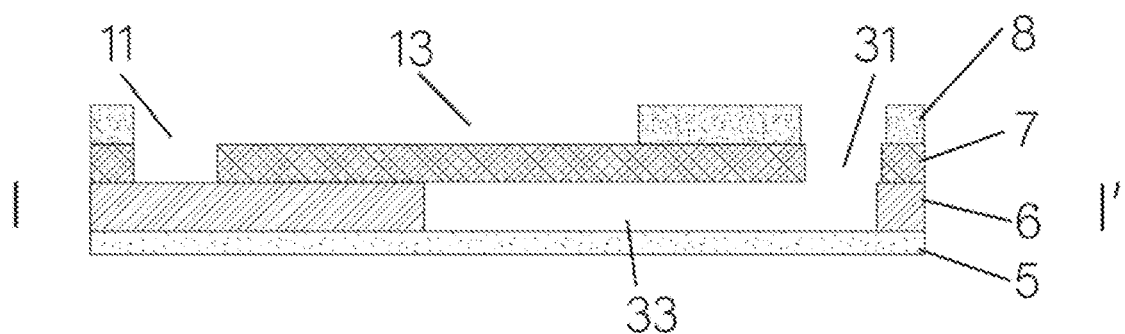
FIG. 26 is a schematic cross-sectional view of II' in FIG. 24.

For another example, as shown in FIG. 24-26, in another specific embodiment of the present disclosure, multiple rows of molecular detection units (only two rows of molecular detection units are shown in FIG. 24), multiple common sample flow channels and multiple common buffer flow channels can be arranged in the molecular detection array, and the number of common sample flow channels in the molecular detection array is less than the number of rows of molecular detection units in the molecular detection array, and the number of common buffer flow channels is equal to the number of rows of molecular detection units in the molecular detection array; a common sample flow channel can be shared by multiple molecular detection units in at least two rows of molecular detection units, for example, the two or more rows of molecular detection units in the molecular detection array share a common sample flow channel 13, and each molecular detection unit in each row of molecular detection units shares a common buffer flow channel 33.

Figure 21:
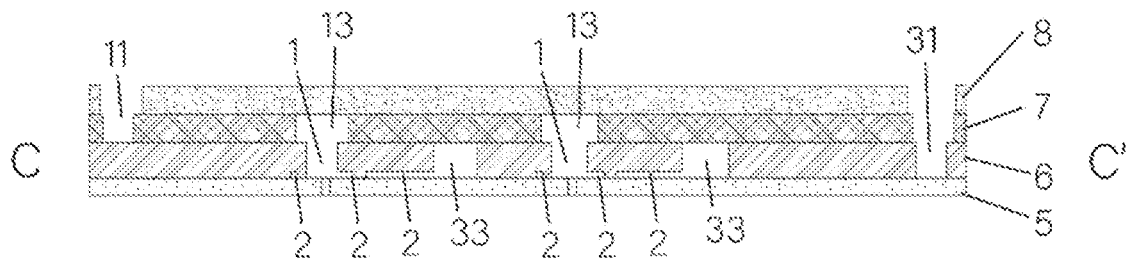
FIG. 21 is a first schematic cross-sectional view of CC' in FIG. 20.
Figure 22:
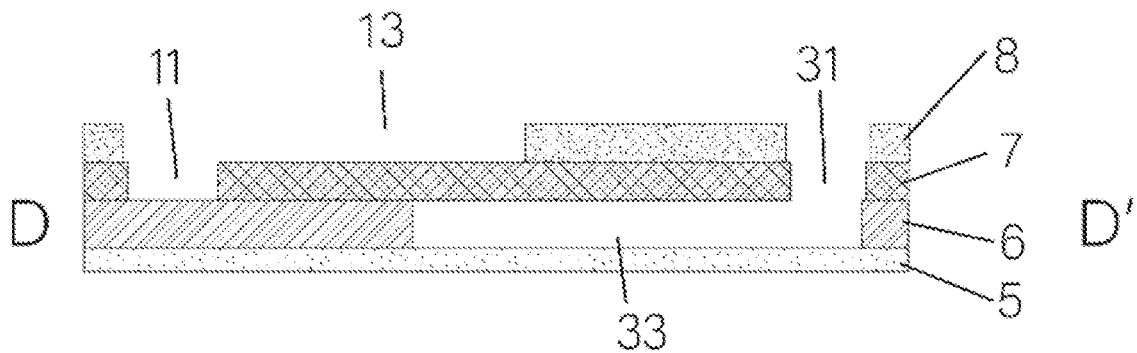
FIG. 22 is a schematic cross-sectional view of DD' in FIG. 20.

In another specific embodiment of the present disclosure, it is assumed that n (n≥2) rows of molecular detection units are arranged in a molecular detection array (for example, only n=2 is shown in FIG. 24, that is, the case of two rows of molecular detection units), and the sample flow channels of each molecular detection unit in n rows are communicated with each other as a common sample flow channel 13 according to their respective arrangement sequences, and the buffer flow channels of each molecular detection unit in each row are communicated with each other as a common buffer flow channel 33 according to their respective arrangement sequences, then only one common sample flow channel 13 and n buffer flow channels 33 can be arranged in the molecular detection array. It can be seen from the cross-section shown in FIG. 25 that the difference from the embodiment shown in FIG. 21 is that the common sample flow channel 13 is also formed in the third structural layer 8, and the range formed in the third structural layer 8 covers multiple rows (for example, n rows, n≥2) of molecular detection units. Therefore, all the n rows of molecular detection units in the molecular detection array share the same common sample flow channel 13, but the n rows of molecular detection units respectively use their corresponding common buffer flow channels 33. One common sample flow channel 13 uses two sample access holes 11, and n common buffer flow channels 33 share two buffer access holes 31. The technical effect of this embodiment is to increase the volume of the common sample flow channel 13.

In addition, in the technical solution of the present disclosure, multiple common sample flow channels and multiple common buffer flow channels can also be preset according to the needs of actual application scenarios, and the number of common sample flow channels is less than the number of rows of molecular detection units in the molecular detection array, and the number of common buffer flow channels is equal to the number of rows of molecular detection units in the molecular detection array.

For example, as an example, in another specific embodiment of the present disclosure, n (n≥2) rows of molecular detection units, m (m<n) common sample flow channels and n common buffer flow channels can also be arranged in the molecular detection array. Therefore, the number of common sample flow channels in the molecular detection array is less than the number of rows of molecular detection units in the molecular detection array, and the number of common buffer flow channels in the molecular detection array is equal to the number of rows of molecular detection units in the molecular detection array; at least one common sample flow channel can be shared by multiple molecular detection units in at least two rows of molecular detection units.

For example, assuming n=3, m=2, that is, the molecular detection array is provided with 3 rows of molecular detection units, 2 common sample flow channels and 3 common buffer flow channels, then the 2 rows of molecular detection units in the molecular detection array can share one of the common sample flow channels, while the remaining row of molecular detection units uses another common sample flow channel; the molecular detection units in the same row share the corresponding common buffer flow channels, namely the 3 common buffer flow channels correspond to the 3 rows of molecular detection units respectively.

For another example, assuming n=4, m=2, that is, the molecular detection array is provided with 4 rows of molecular detection units, 2 common sample flow channels and 4 common buffer flow channels, then the 2 rows of molecular detection units in the molecular detection array can share one of the common sample flow channels, while the remaining 2 rows of molecular detection units share another common sample flow channel; or, the 3 rows of molecular detection units in the molecular detection array can share one of the common sample flow channels, and the remaining row of molecular detection units share another common sample flow channel; each molecular detection unit in the same row shares the corresponding common buffer flow channel respectively, that is, the 4 common buffer flow channels correspond to the 4 rows of molecular detection units respectively.

In addition, in other specific embodiments of the present disclosure, when the values of n and m are other values, the corresponding relationship between each common sample flow channel and common buffer flow channel and each row of molecular detection units can be specifically set with reference to the above-mentioned specific embodiments, and will not be listed here.

Figure 27:
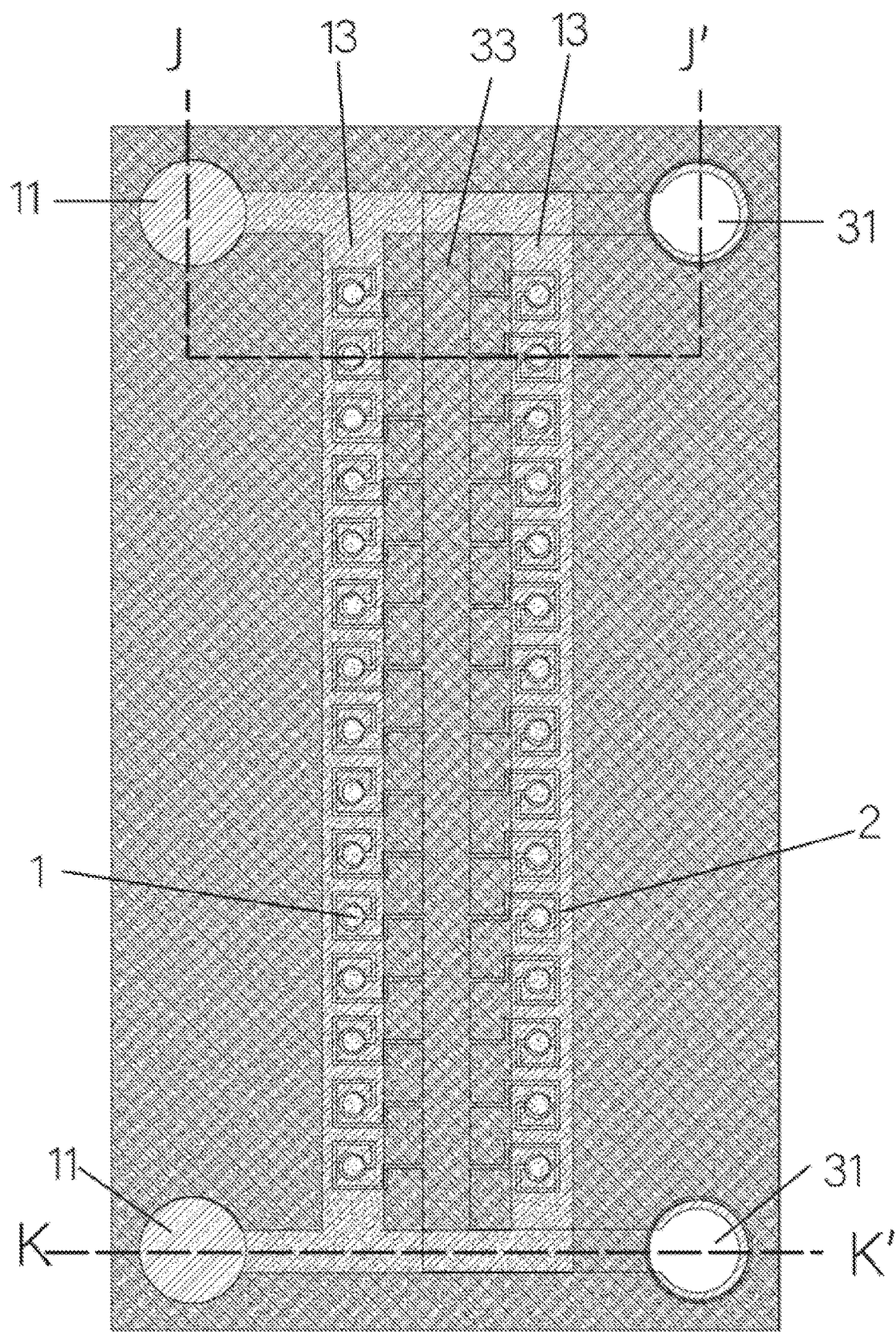
FIG. 27 is a schematic structural diagram of a molecular detection array in another specific embodiment of the present disclosure.
Figure 28:
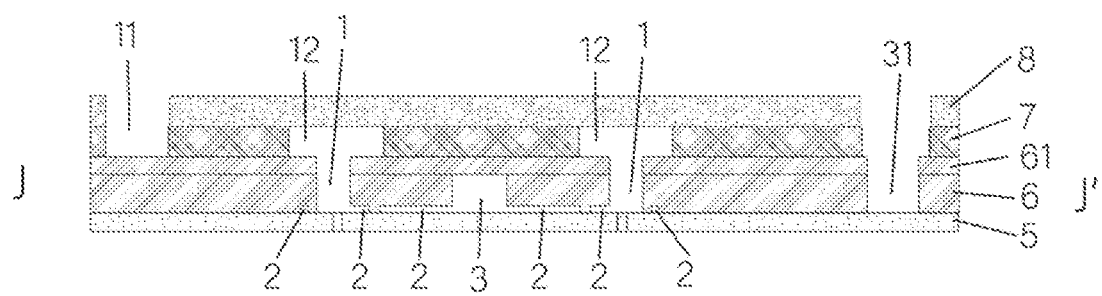
FIG. 28 is a schematic cross-sectional view of JJ' in FIG. 27.
Figure 29:
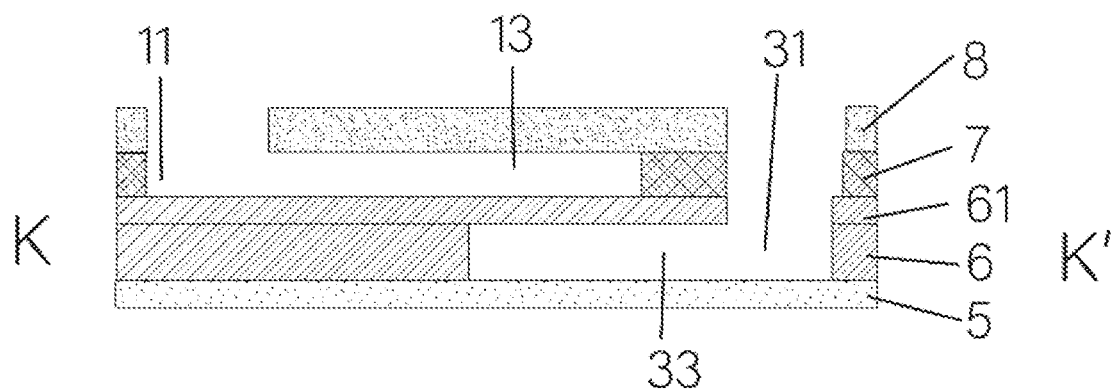
FIG. 29 is a schematic cross-sectional view of KK' in FIG. 27.

For another example, as shown in FIGS. 27-29, in another specific embodiment of the present disclosure, multiple rows of molecular detection units (only two rows of molecular detection units are shown in FIG. 27), multiple common sample flow channels and multiple common buffer flow channels can be arranged in the molecular detection array, and the number of common sample flow channels in the molecular detection array is equal to the number of rows of molecular detection units in the molecular detection array, and the number of common buffer flow channels is less than the number of rows of molecular detection units in the molecular detection array; a common buffer flow channel can be shared by multiple molecular detection units in two adjacent rows of molecular detection units, for example, the multiple molecular detection units in the molecular detection array can be arranged in two rows; the molecular detection units in each row share a common sample flow channel 13, and the two rows of molecular detection units share a common buffer flow channel 33.

In this specific embodiment, two rows of molecular detection units are arranged in the molecular detection array, and two common sample flow channels 13 and one common buffer flow channel 33 are arranged in the molecular detection array.

Therefore, the two rows of molecular detection units in the molecular detection array respectively use their corresponding common sample flow channels 13, but the two rows of molecular detection units share the same common buffer flow channel 33. 2 common sample flow channels 13 share two sample access holes 11, and 1 common buffer flow channel 33 uses two buffer access holes 31. The technical effect of this embodiment is to reduce the number of common buffer flow channels 33, so that the number of molecular detection units included in the molecular detection array can be increased, and the flux can be further improved.

In addition, in the technical solution of the present disclosure, multiple common sample flow channels and multiple common buffer flow channels can also be preset according to the needs of actual application scenarios, and the number of common sample flow channels is equal to the number of rows of molecular detection units in the molecular detection arrays, while the number of common buffer flow channels is less than the number of rows of molecular detection units in the molecular detection array, those skilled in the art can imagine that it can be realized by freely combining the embodiments shown in FIG. 19 to FIG. 29.

For example, as an example, in another specific embodiment of the present disclosure, n (n≥2) rows of molecular detection units, n common sample flow channels and m (m<n) common buffer flow channels can also be arranged in the molecular detection array. Therefore, the number of common sample flow channels in the molecular detection array is equal to the number of rows of molecular detection units in the molecular detection array, while the number of common buffer flow channels in the molecular detection array is less than the number of rows of molecular detection units in the molecular detection array; at least one common buffer flow channel can be shared by multiple molecular detection units in two adjacent rows of molecular detection units.

For example, assuming n=3, m=2, that is, the molecular detection array is provided with 3 rows of molecular detection units, 3 common sample flow channels and 2 common buffer flow channels, then the 2 rows of molecular detection units in the molecular detection array can share one of the common buffer flow channels, while the remaining row of molecular detection units uses another common buffer flow channel; the molecular detection units in the same row share the corresponding common sample flow channels, namely the 3 common sample flow channels correspond to the 3 rows of molecular detection units respectively.

For another example, assuming n=4, m=2, that is, the molecular detection array is provided with 4 rows of molecular detection units, 4 common sample flow channels and 2 common buffer flow channels, then the 2 rows of molecular detection units in the molecular detection array can share one of the common buffer flow channels, while the remaining 2 rows of molecular detection units share another common buffer flow channel; or, the 3 rows of molecular detection units in the molecular detection array can share one of the common buffer flow channel, and the remaining row of molecular detection units share another common buffer flow channel (for example, a common buffer flow channel layer can be arranged in the molecular detection chip, and the common buffer flow channel layer can be located above or below the buffer flow channel of each molecular detection unit, so that the above-mentioned two common buffer flow channels can be respectively formed in the buffer flow channel layer; in addition, as shown in FIG. 28 and FIG. 29, a structural layer 61 can be added between the first structural layer 6 and the second structural layer 7 to realize liquid isolation between the common sample flow channel 13 and the common buffer flow channel 33); each molecular detection unit in the same row shares the corresponding common sample flow channel respectively, that is, the 4 common sample flow channels correspond to the 4 rows of molecular detection units respectively.

In addition, in other specific embodiments of the present disclosure, when the values of n and m are other values, the corresponding relationship between each common sample flow channel and common buffer flow channel and each row of molecular detection units can be specifically set with reference to the above-mentioned specific embodiments, and will not be listed here.

In addition, in the technical solution of the present disclosure, multiple common sample flow channels and multiple common buffer flow channels can also be preset according to the needs of actual application scenarios, and the number of common sample flow channels is less than the number of rows of molecular detection units in the molecular detection array, and the number of common buffer flow channels is also less than the number of rows of molecular detection units in the molecular detection array.

For example, as an example, in another specific embodiment of the present disclosure, n (n≥2) rows of molecular detection units, m (m<n) common sample flow channels and k (k<n) common buffer flow channels can also be arranged in the molecular detection array. Therefore, the number of common sample flow channels and the number of common buffer flow channels in the molecular detection array are less than the number of rows of molecular detection units in the molecular detection array. At least one common sample flow channel can be shared by multiple molecular detection units in at least two rows of molecular detection units, and at least one common buffer flow channel can be shared by multiple molecular detection units in two adjacent rows of molecular detection units.

For example, assuming n=3, m=2, k=2, that is, the molecular detection array is provided with 3 rows of molecular detection units, 2 common sample flow channels and 2 common buffer flow channels, then the 2 rows of molecular detection units in the molecular detection array can share one of the common sample flow channels, while the remaining row of molecular detection unit uses another common sample flow channel; at the same time, the 2 rows of molecular detection units in the molecular detection array share one of the common buffer flow channels, while the remaining row of molecular detection units uses another common buffer flow channel.

For another example, assuming n=4, m=2, k=2, that is, the molecular detection array is provided with 4 rows of molecular detection units, 2 common sample flow channels and 2 common buffer flow channels, then the 2 rows of molecular detection units in the molecular detection array can share one of the common sample flow channels, while the remaining 2 rows of molecular detection units share another common sample flow channel; or, the 3 rows of molecular detection units in the molecular detection array can share one of the common sample flow channels, and the remaining row of molecular detection units share another common sample flow channel; at the same time, the 2 rows of molecular detection units in the molecular detection array can share one of the common buffer flow channel, and the remaining 2 rows of molecular detection units share another common buffer flow channel; or, the 3 rows of molecular detection units in the molecular detection array can share one of the common buffer flow channels, and the remaining row of molecular detection units share another common buffer flow channel.

In addition, in other specific embodiments of the present disclosure, when the values of n, m, and k are other values, the corresponding relationship between each common sample flow channel and common buffer flow channel and each row of molecular detection units can be specifically set with reference to the above-mentioned specific embodiments, and will not be listed here.

In addition, in the technical solution of the present disclosure, the number of molecular detection units in each row of molecular detection units in the molecular detection array can also be flexibly set according to the needs of actual application scenarios.

For example, as an example, in a specific embodiment of the present disclosure, when the molecular detection array includes multiple rows of molecular detection units, the number of molecular detection units in each row of molecular detection units can be equal, as shown in FIG. 20, FIG. 24 and FIG. 27.

For another example, as an example, in another specific embodiment of the present disclosure, when the molecular detection array includes multiple rows of molecular detection units, the number of molecular detection units in each row of molecular detection units may not be equal.

In addition, in the technical solution of the present disclosure, the number and specific positions of the first driving electrodes and the second driving electrodes in the molecular detection chip can be flexibly set according to the needs of actual application scenarios.

Figure 30:
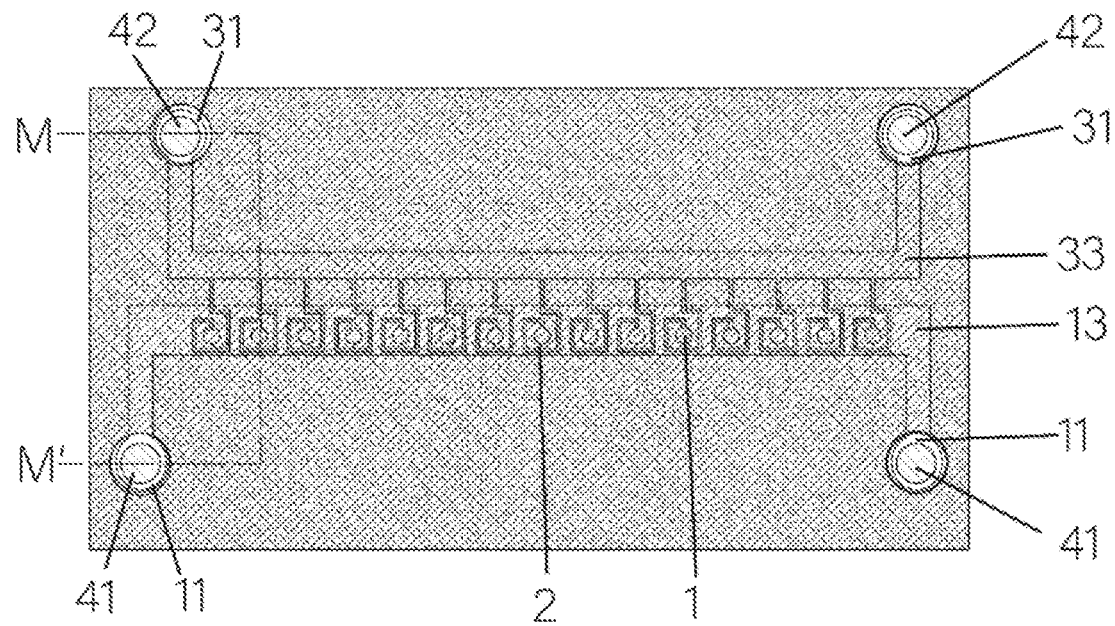
FIG. 30 is a schematic structural diagram of a molecular detection array in another specific embodiment of the present disclosure.
Figure 31:
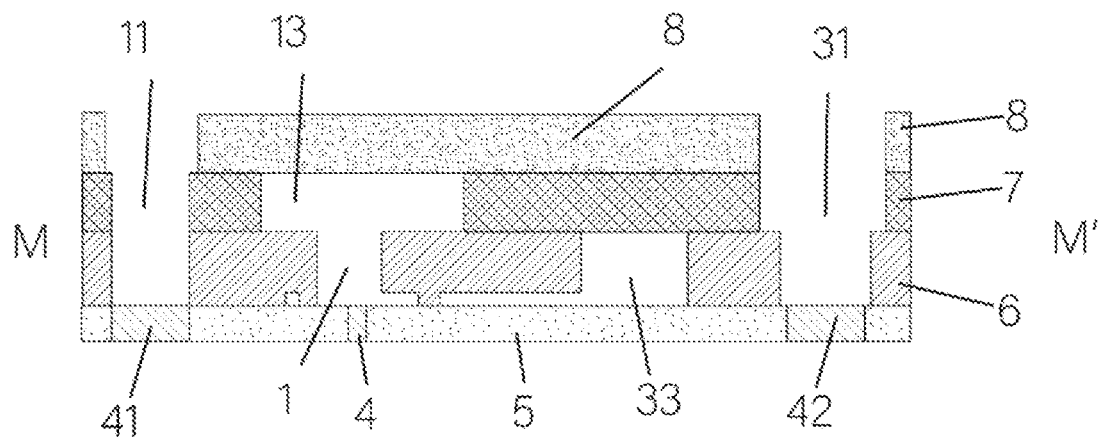
FIG. 31 is a schematic cross-sectional view of MM' in FIG. 30.

For example, as shown in FIG. 30 and FIG. 31, in a specific embodiment of the present disclosure, two first driving electrodes 41 and two second driving electrodes 42 can be further provided in the molecular detection chip; the first driving electrode 41 and the second driving electrode 42 can be arranged at the bottom of the sample access hole 11 and the buffer access hole 31 respectively. At this time, it is equivalent to setting a total of two first driving electrodes 41 and two second driving electrodes 42 in the molecular detection chip. Each first driving electrode 41 can communicate with a sample access hole 11, so that a corresponding voltage can be applied to the liquid in the sample flow channel 12 through the first driving electrode 41; and each second driving electrode 42 can communicate with a buffer access hole 31, so that a corresponding voltage can be applied to the liquid in the buffer flow channel 3 through the second driving electrode 42.

In addition, as an example, as shown in FIG. 31, in a specific embodiment of the present disclosure, the first driving electrode 41 and the second driving electrode 42 may be arranged in the substrate 5. One end of the first driving electrode 41 and the second driving electrode 42 can be exposed by the first structural layer 6 (for example, through holes that can expose the first driving electrode 41 and the second driving electrode 42 can be respectively provided in the substrate 5), so that one end of the first driving electrode 41 communicates with the sample access hole 11, and one end of the second driving electrode 42 communicates with the buffer access hole 31.

At this time, the sample access hole 11 and the buffer access hole 31 can penetrate through the first structural layer 6, the second structural layer 7 and the third structural layer 8, so that the first driving electrode 41 can be communicated with the liquid in the common sample flow channel, and the second driving electrode 42 can be communicated with the liquid in the common buffer flow channel 33.

The advantage of setting the driving electrodes on the substrate in this embodiment is that it can further integrate the circuit onto the chip, reducing the trouble of external connections (such as the interfaces 91, 92, so that the interfaces 91, 92 only need to complete the liquid passage).

Figure 32:
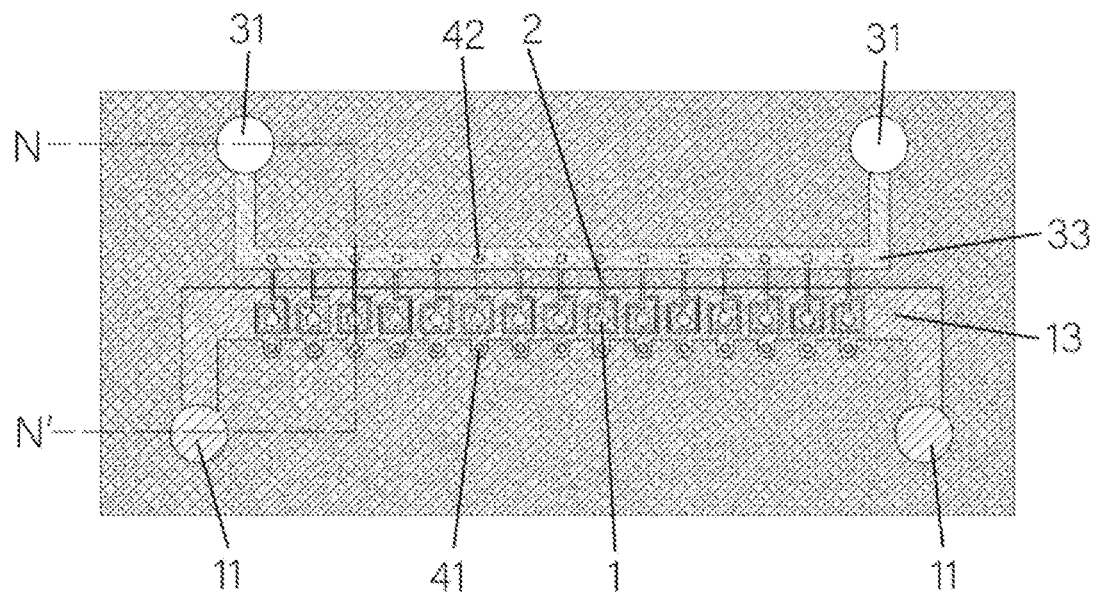
FIG. 32 is a schematic structural diagram of a molecular detection array in another specific embodiment of the present disclosure.
Figure 33:
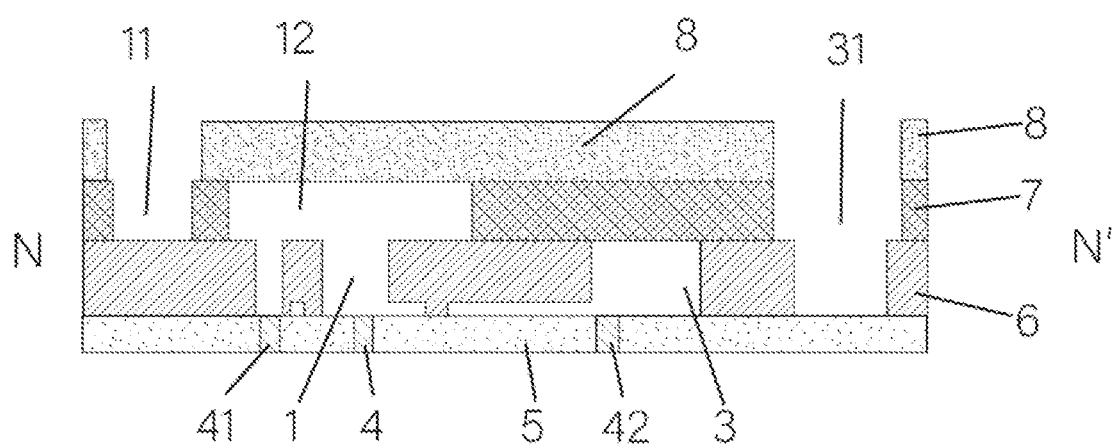
FIG. 33 is a schematic cross-sectional view of NN' in FIG. 32.

In addition, as an example, as shown in FIG. 32 and FIG. 33, in another specific embodiment of the present disclosure, each molecular detection unit in the molecular detection chip is provided with a first driving electrode 41 and a second driving electrode 42; the first driving electrode 41 and the second driving electrode 42 can be respectively arranged at the bottom of the sample flow channel 12 and the bottom of the buffer flow channel 3 of the molecular detection unit. At this time, it is equivalent to setting a first driving electrode 41 and a second driving electrode 42 for each molecular detection unit. Therefore, each first driving electrode 41 can be directly communicated with the sample flow channel 12, so that a corresponding voltage can be applied to the liquid in the sample flow channel 12 through the first driving electrode 41; and each second driving electrode 42 can be directly communicated with the buffer flow channel 3, so that a corresponding voltage can be applied to the liquid in the buffer flow channel 3 through the second driving electrode 42.

In addition, as an example, as shown in FIG. 33, in a specific embodiment of the present disclosure, the first driving electrode 41 and the second driving electrode 42 may be arranged in the substrate 5. One end of the first driving electrode 41 can be exposed to the sample channel 12 in the second structural layer 7 by the first structural layer 6 (for example, through holes that can expose the first driving electrodes 41 can be respectively provided in the substrate 5), so that one end of the first driving electrode 41 communicates with the sample flow channel 12, and one end of the second driving electrode 42 can be exposed to the buffer flow channel 3 in the first structural layer 6, so that one end of the second driving electrode 42 communicates with the sample flow channel 12.

The technical problem solved by this embodiment is: in the embodiment such as FIGS. 30-31, due to the smaller size of the driving electrodes 41, 42 compared to the molecular detection array, the driving electrodes are relatively close to some molecular detection units but farther apart from other molecular detection units. For example, as shown in FIG. 30, the molecular detection units on the left or right sides are closer to the driving electrodes than the molecular detection unit located in the center. When more molecular detection units are included in the molecular detection array, as the distance between the detection units and the driving electrodes increases, the resistance caused by the common sample flow channel 13 and the common buffer flow channel 33 will also increase. In order to minimize the impact of the increase in the resistance of the common channel, a pair of driving electrodes in the substrate can be designed on both sides of each detection unit.

The technical effect of this embodiment is that, in the embodiment of FIG. 32, each pair of driving electrodes 41, 42 is positioned substantially equidistant from the corresponding molecular detection unit, the voltage drop caused by the resistance of the conductive fluid is becomes substantially the same, and the variation in voltage between different molecular detection units is thus significantly reduced.

In addition, in the technical solution of the present disclosure, the upper planes of the first driving electrodes 41 and the second driving electrodes 42 can be flush with the upper plane of the substrate 5 (for example, as shown in FIGS. 10, 11, 31 and 33), or may be higher than the upper plane of the substrate 5; or, the first driving electrode 41 and the second driving electrode 42 may also be arranged on the upper plane of the substrate 5, and connected to corresponding circuit structures through metal leads arranged in the substrate 5.

In addition, in the technical solution of the present disclosure, according to the needs of actual application scenarios, any arrangement of the first driving electrode and the second driving electrode in the above-mentioned specific embodiments (for example, multiple specific embodiments shown in FIG. 30-FIG. 34) can be applied to any form of molecular detection chip including the specific embodiments shown in FIG. 19-FIG. 29 above, and will not be listed here.

In addition, in the technical solution of the present disclosure, a method for preparing a molecular detection chip is also proposed.

Figure 34:
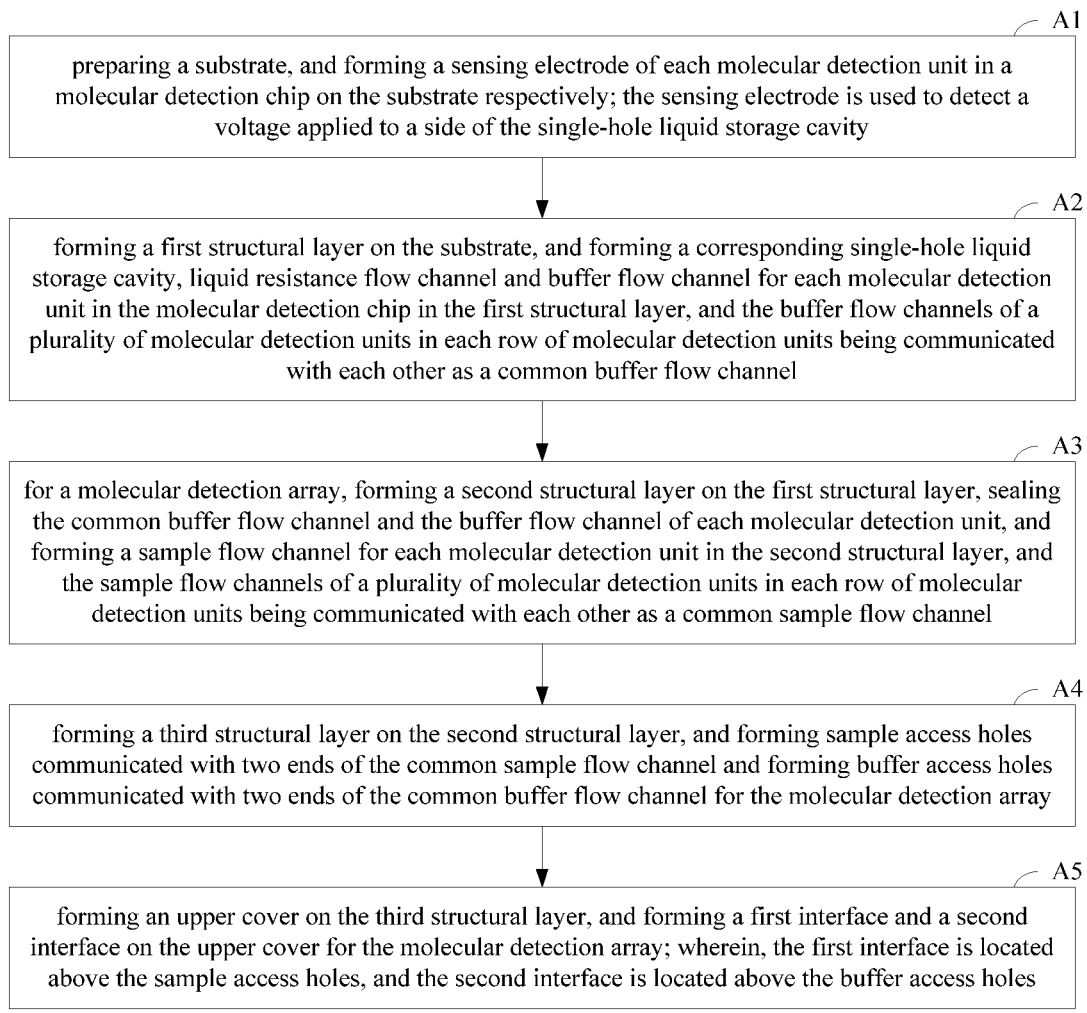
FIG. 34 is a schematic flowchart of a method for preparing a molecular detection chip in a specific embodiment of the present disclosure.

For example, as an example, as shown in FIG. 34, in a specific embodiment of the present disclosure, the method for preparing the above-mentioned molecular detection chip may include the following steps:

Step A1, preparing a substrate, and forming sensing electrodes of each molecular detection unit in a molecular detection chip on the substrate respectively.

Figure 35:
FIG. 35 is a first schematic diagram of the preparation process of the molecular detection chip in a specific embodiment of the present disclosure.

For example, as an example, as shown in FIG. 35, in a specific embodiment of the present disclosure, a substrate layer (ie, the substrate 5) may first be manufactured through a semiconductor process, and the substrate layer may be used to contain the circuit structure required by the device. In addition, in the process of manufacturing the substrate 5, the sensing electrodes 4 of the molecular detection units in the molecular detection chip can be respectively formed in the substrate 5 by means of semiconductor technology. The sensing electrodes 4 can be connected to different types of circuit boards or circuit chips through different semiconductor packaging methods, which will not be repeated here.

In addition, in the technical solution of the present disclosure, the upper plane of the sensing electrode 4 may be flush with the upper plane of the substrate 5 (for example, as shown in FIG. 2, FIG. 3, FIG. 5-8, FIG. 10, FIG. 11, FIG. 13, FIG. 15, FIG. 17, FIG. 18, FIG. 21, FIG. 23, FIG. 25, FIG. 28, FIG. 31, FIG. 33, and FIG. 35-41), or may be higher than the upper plane of the substrate 5; or, the sensing electrodes 4 can also be arranged on the upper plane of the substrate 5 and connected to different types of circuit boards or circuit chips through metal leads arranged in the substrate 5.

Step A2, forming a first structural layer on the substrate, and forming a corresponding single-hole liquid storage cavity, liquid resistance flow channel and buffer flow channel for each molecular detection unit in the molecular detection chip in the first structural layer, and the buffer flow channels of a plurality of molecular detection units in each row of molecular detection units being communicated with each other as a common buffer flow channel.

In this step, the first structural layer 6 will be formed on the substrate 5 first, and then a corresponding single-hole liquid storage cavity 1, liquid resistance flow channel 2 and buffer flow channel 3 will be formed in the first structural layer 6 for each molecular detection unit in the molecular detection chip; moreover, the buffer flow channels 3 of multiple molecular detection units in each row of molecular detection units can be connected to each other as a common buffer flow channel 33.

In addition, as an example, in a specific embodiment of the present disclosure, the bottoms of two buffer access holes that communicate with two ends of the common buffer channel 33 can be further formed in the first structural layer 6 for the molecular detection array in the molecular detection chip.

In addition, in the technical solution of the present disclosure, various implementation manners may be used to realize the above step A2. The following will introduce the technical solutions of the present disclosure by taking several specific implementation manners as examples.

Figure 53:
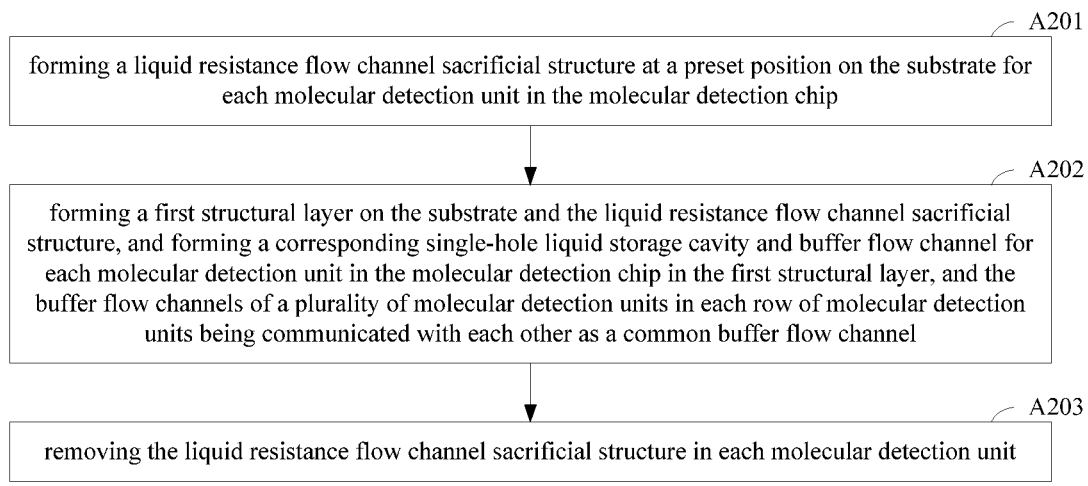
FIG. 53 is a schematic flowchart of a method for preparing a molecular detection chip in another specific embodiment of the present disclosure.

For example, as an example, as shown in FIG. 53, in a specific embodiment of the present disclosure, the above step A2 may include the following steps.

Step A201, forming a liquid resistance flow channel sacrificial structure at a preset position on the substrate for each molecular detection unit in the molecular detection chip.

Figure 36:
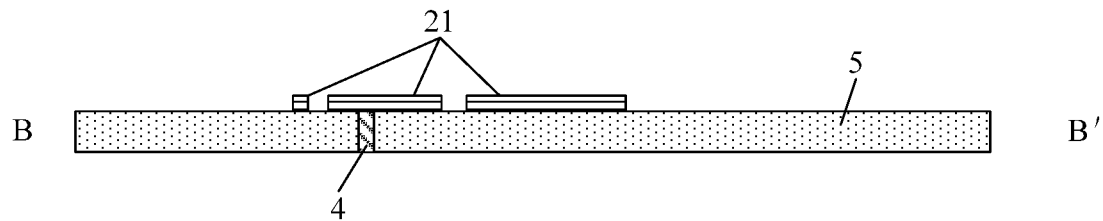
FIG. 36 is a second schematic diagram of the preparation process of the molecular detection chip in a specific embodiment of the present disclosure.

For example, as an example, as shown in FIG. 36, in a specific embodiment of the present disclosure, for each molecular detection unit in the molecular detection chip, some kind of pattern transfer method (for example, electron beam exposure or laser direct writing etc.) and some kind of material deposition process (for example, physical vapor deposition or chemical vapor deposition, etc.) can be used to form a liquid resistance flow channel sacrificial structure 21 at a preset position on the substrate 5 (that is, the position where the liquid resistance flow channel 2 of each molecular detection unit needs to be formed).

For example, as an example, in a specific embodiment of the present disclosure, the liquid resistance flow channel sacrificial structure 21 may be made of sacrificial material such as amorphous silicon.

Step A202, forming a first structural layer on the substrate and the liquid resistance flow channel sacrificial structure, and forming a corresponding single-hole liquid storage cavity and buffer flow channel for each molecular detection unit in the molecular detection chip in the first structural layer, and the buffer flow channels of a plurality of molecular detection units in each row of molecular detection units being communicated with each other as a common buffer flow channel.

Figure 37:
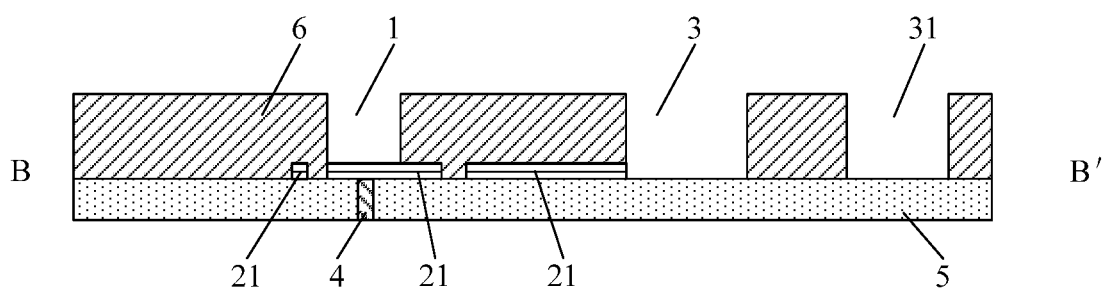
FIG. 37 is a third schematic diagram of the preparation process of the molecular detection chip in a specific embodiment of the present disclosure.

For example, as an example, as shown in FIG. 37, in a specific embodiment of the present disclosure, for each molecular detection unit in the molecular detection chip, some kind of material deposition process (for example, physical vapor deposition or chemical vapor deposition etc.) can be used to form the first structural layer 6 covering the substrate 5 and the liquid resistance flow channel sacrificial structure 21; then, through some kind of pattern transfer method (for example, photolithography, etc.) and some kind of etching process (for example, reactive ion etching etc.) can be used to form the single-hole liquid storage cavity 1 and the buffer flow channel 3 of each molecular detection unit in the first structural layer 6; moreover, it is also possible to make the buffer flow channels 3 of multiple molecular detection units in each row of molecular detection units communicate with each other as a common buffer flow channel 33.

In addition, as an example, in a specific embodiment of the present disclosure, it is also possible to further form the bottoms of the two buffer access hole 31 communicate with two ends of the common buffer flow channel 33 in the first structural layer 6 for the molecular detection array in the molecular detection chip.

Step A203, removing the liquid resistance flow channel sacrificial structure in each molecular detection unit.

Figure 38:
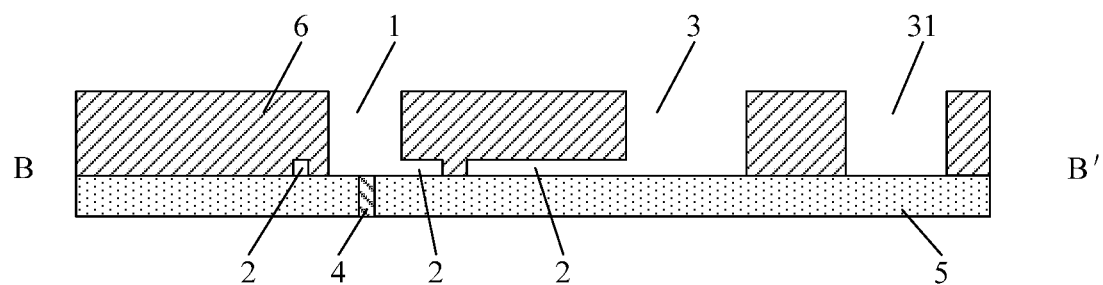
FIG. 38 is a fourth schematic diagram of the preparation process of the molecular detection chip in a specific embodiment of the present disclosure.

For example, as an example, as shown in FIG. 38, in a specific embodiment of the present disclosure, some kind of etching process (for example, xenon fluoride silicon etching, etc.) can be used to remove the liquid resistance flow channel sacrificial structure 21 in each molecular detection unit, so as to form a liquid resistance flow channel 2 connecting the single-hole liquid storage cavity 1 and the buffer flow channel 3, so that two sets of microchannel systems (the sample microchannel system and the buffer microchannel system) can be connected.

Therefore, through the above-mentioned steps A201~A203, the above-mentioned first structural layer 6 can be formed, and the single-hole liquid storage cavity 1, the liquid resistance flow channel 2 and the buffer flow channel 3 of each molecular detection unit in the molecular detection chip can be formed in the first structural layer 6, and the buffer flow channels 3 of multiple molecular detection units in each row of molecular detection units communicate with each other as a common buffer flow channel 33. In addition, the bottoms of the two buffer access holes 31 communicating with two ends of the common buffer flow channel 33 can be further formed in the first structural layer 6 for the molecular detection array.

In the above-mentioned steps A201~A203, the liquid resistance flow channel is realized by first adding a sacrificial layer material (that is, the liquid resistance flow channel sacrificial structure) at a preset position on the substrate, and then removing the sacrificial layer material.

In the technical solution of the present disclosure, the above-mentioned liquid resistance flow channel can also be realized in other ways.

Figure 54:
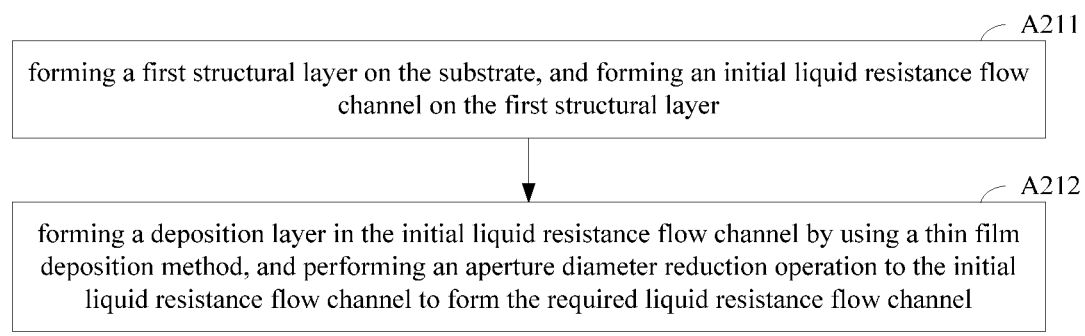
FIG. 54 is a schematic flowchart of a method for preparing a molecular detection chip in another specific embodiment of the present disclosure.

For example, as an example, as shown in FIG. 54, in a specific embodiment of the present disclosure, the liquid resistance flow channel 2 may be formed through the following steps.

Step A211, forming a first structural layer on the substrate, and forming an initial liquid resistance flow channel on the first structural layer.

Figure 42:
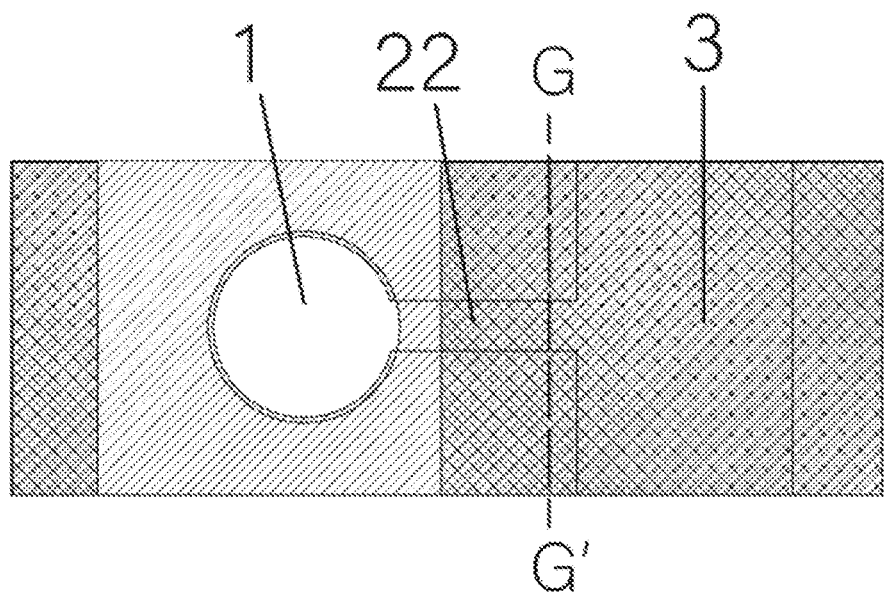
FIG. 42 is a schematic diagram of forming an initial liquid resistance flow channel in a specific embodiment of the present disclosure.
Figure 43:
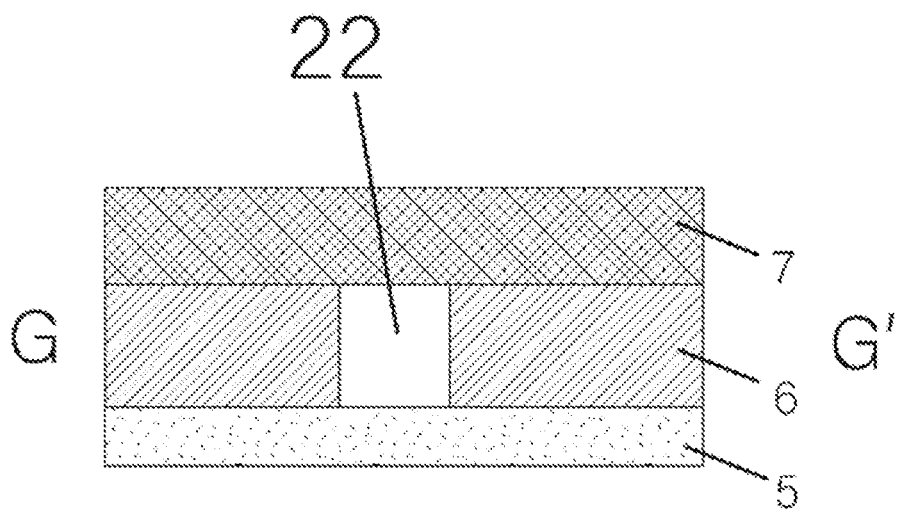
FIG. 43 is a schematic cross-sectional view of GG' in FIG. 42.

In the technical solution of the present disclosure, the first structural layer 6 can be formed on the substrate 5 first, and then the initial liquid resistance flow channel 22 is formed on the first structural layer 6; the two ends of the initial liquid resistance flow channel 22 are respectively connected to the single-hole liquid storage cavity 1 and the buffer flow channel 3, as shown in FIG. 42 and FIG. 43.

The height and width of the initial liquid resistance flow channel 22 may be greater than the required height and width of the liquid resistance flow channel 2, so that the initial liquid resistance flow channel 22 can be formed by using a graphical technique with a larger feature size.

Step A212, forming a deposition layer in the initial liquid resistance flow channel by using a thin film deposition method, and performing an aperture diameter reduction operation to the initial liquid resistance flow channel to form the required liquid resistance flow channel.

Figure 44:
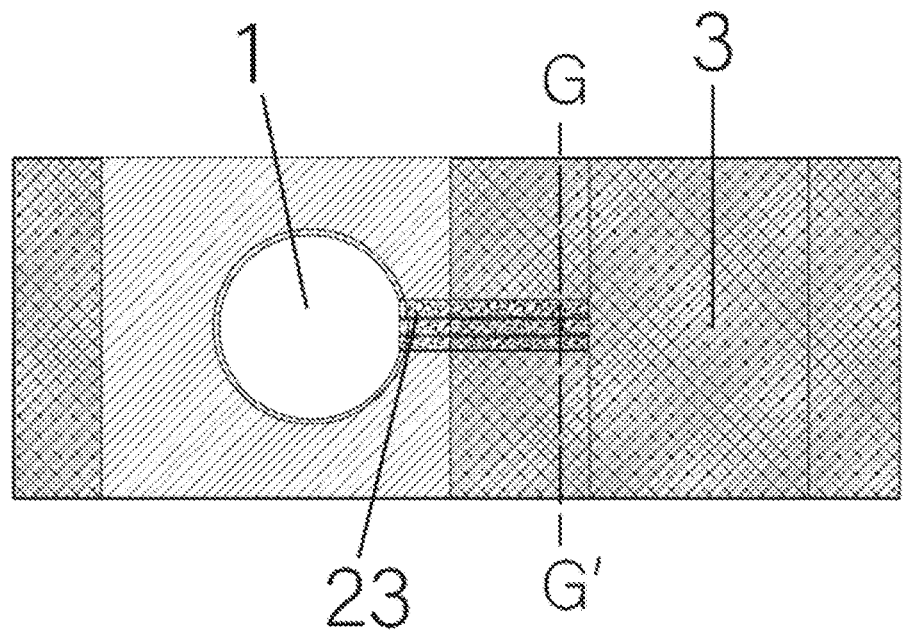
FIG. 44 is a schematic diagram of performing an aperture diameter reduction operation in a specific embodiment of the present disclosure.
Figure 45:
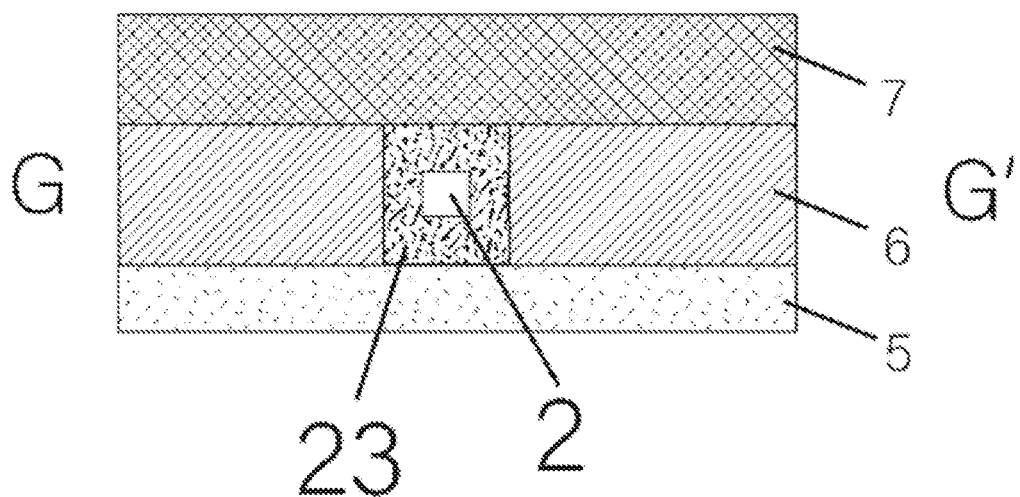
FIG. 45 is a schematic cross-sectional view of GG' in FIG. 44.

For example, as an example, as shown in FIG. 44 and FIG. 44, in another specific embodiment of the present disclosure, a thin film deposition method (for example, atomic layer deposition method) with better conformality can be used to make a corresponding deposition layer 23 in the initial liquid resistance flow channel 22, so as to perform aperture diameter reduction operation to the initial liquid resistance flow channel 22 to form the required liquid resistance flow channel.

After the aperture diameter reduction operation is completed, the height and width of the initial liquid resistance flow channel 22 are reduced by the formed deposition layer 23, so that the cross-sectional area of the initial liquid resistance flow channel 22 is also correspondingly reduced, so that the resistance value of the liquid resistance flow channel 2 formed after the aperture diameter reduction operation can meet the preset requirements.

Through the above step A211 and step A212, the required liquid resistance flow channel can be formed.

Through simulation calculation, it can be known that the size of the liquid resistance is proportional to the liquid resistivity and the length of the liquid resistance flow channel, and inversely proportional to the cross-sectional area of the liquid resistance flow channel. The change in the cross-sectional area of the liquid flow channel caused by the deposition layer 23 can generally reduce the cross-sectional area of the initial resistance flow channel 22 from about 1 square micron to 0.01 square micron or even 100 square nanometers in the final liquid resistance flow channel 2. Therefore, by using the above method, the resistance value of the liquid resistance flow channel can be increased to one hundred times or even ten thousand times of the initial state, thereby providing some engineering convenience for the design and manufacture of the liquid resistance flow channel.

For another example, as an example, in another specific embodiment of the present disclosure, the above-mentioned liquid resistance flow channel can also be realized by etching the substrate or the first structural layer, and then bonding and assembling the two.

Step A3, for a molecular detection array, forming a second structural layer on the first structural layer, sealing the common buffer flow channel and the buffer flow channel of each molecular detection unit, and forming a sample flow channel for each molecular detection unit in the second structural layer, and the sample flow channels of a plurality of molecular detection units in each row of molecular detection units being communicated with each other as a common sample flow channel.

Figure 39:
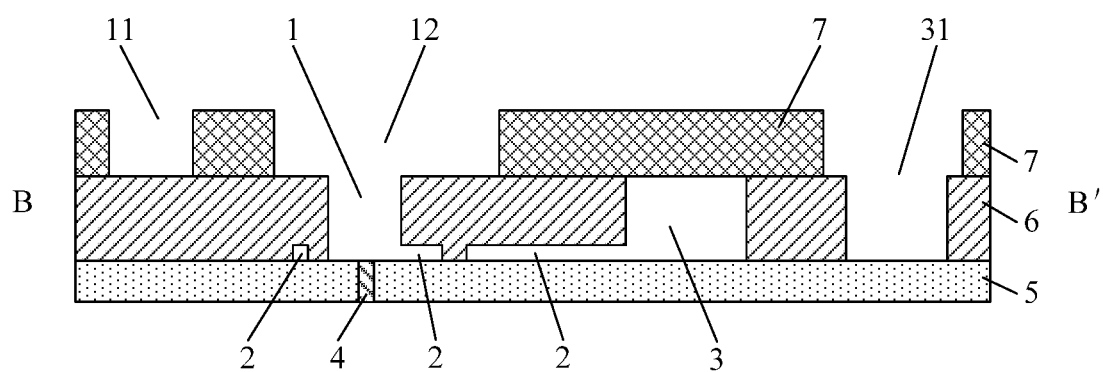
FIG. 39 is a fifth schematic diagram of the preparation process of the molecular detection chip in a specific embodiment of the present disclosure.

For example, as an example, as shown in FIG. 39, in a specific embodiment of the present disclosure, for the molecular detection array in the molecular detection chip, the corresponding semiconductor process (for example, dry film lithography process, etc.) can be used to form a second structural layer 7 on the structural layer 6, and a sample flow channel 12 is formed for each molecular detection unit in the second structural layer 7, so that the single-hole liquid storage cavity 1 communicates with the sample flow channel 12 (this, the sample flow channel 12 is located at the top of the single-hole liquid storage cavity 1); moreover, the sample flow channels 12 of multiple molecular detection units in each row of molecular detection units can also be connected to each other as a common sample flow channel 13. At the same time, the second structural layer 7 covers the top of the common buffer flow channel 33 and the buffer flow channel 3 of each molecular detection unit, so as to seal the common buffer flow channel 33 and the buffer flow channel 3 of each molecular detection unit, realizing the overall sealing of the buffer flow channel 3 and the common buffer flow channel 33, so that the single-hole liquid storage cavity 1 and the buffer flow channel 3 can only be connected through the liquid resistance flow channel 2 structurally.

In addition, as an example, in a specific embodiment of the present disclosure, two sample access holes 11 communicating with two ends of the common sample flow channel 13 can be further formed in the second structural layer 7 for the molecular detection array, and the upper parts of the two buffer access holes 31 communicating with two ends of the common buffer flow channel 33 is formed in the second structural layer 7 for the molecular detection array. Therefore, at this time, the buffer access holes 31 located at two ends of the common buffer flow channel 33 actually penetrate the first structural layer 6 and the second structural layer 7.

Step A4, forming a third structural layer on the second structural layer, and forming sample access holes communicated with two ends of the common sample flow channel and forming buffer access holes communicated with two ends of the common buffer flow channel for the molecular detection array.

In the technical solution of the present disclosure, for the molecular detection array in the molecular detection chip, the third structural layer 8 can be formed on the second structural layer 7 through a corresponding semiconductor process (for example, dry film photolithography process, etc.); and then, according to the needs of the actual application scenario, various required structures are formed in the third structural layer 8.

Figure 40:
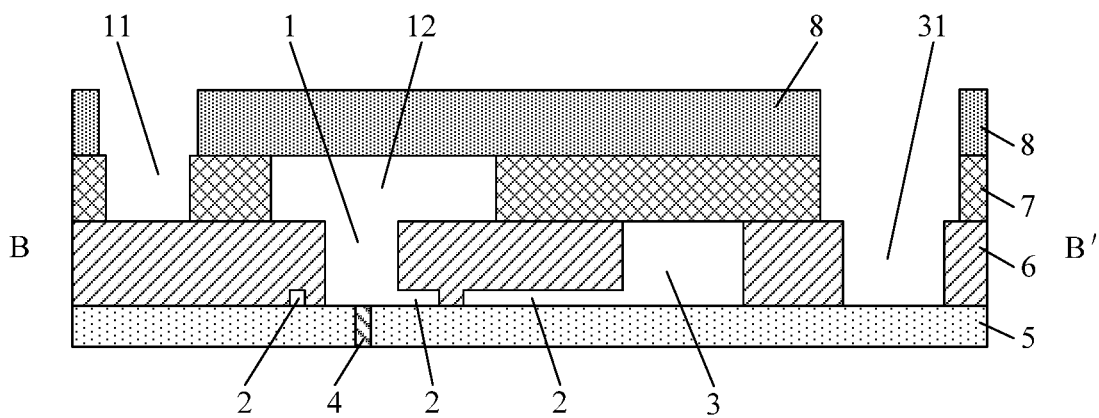
FIG. 40 is a sixth schematic diagram of the preparation process of the molecular detection chip in a specific embodiment of the present disclosure.

For example, as an example, as shown in FIG. 40, in a specific embodiment of the present disclosure, for the molecular detection array in the molecular detection chip, the corresponding semiconductor process (for example, dry film lithography process, etc.) can be used to form a third structural layer 8 in the second structural layer 7, so that the third structural layer 8 covers the top of the common sample flow channel 13 and the sample flow channel 12 of each molecular detection unit, so as to seal the common sample flow channel 13 and the sample flow channel 12 of each molecular detection unit, so as to realize the overall sealing of the sample flow channel 12 and the common sample flow channel 13.

For another example, as shown in FIGS. 24-26, in another specific embodiment of the present disclosure, for the molecular detection array in the molecular detection chip, the third structural layer 8 can also be formed on the second structural layer 7 through a corresponding semiconductor process first, and then the common sample flow channels 13 in the molecular detection array are connected in the third structural layer 8 as a whole. For example, a groove communicating with each common sample flow channel 13 in the molecular detection array can be formed in the third structural layer 8, covering the top of the sample flow channels of multiple rows (for example, two rows) of molecular detection units, so as to communicate with each common sample flow channel 13 as a whole.

In addition, a sample access hole connected to two ends of the common sample flow channel and a buffer access hole connected to two ends of the common buffer flow channel can also be formed in the third structural layer 8 for the molecular detection array.

For example, as shown in FIG. 40, the tops of the two sample access holes 11 communicated with the two ends of the common sample flow channel 13 and the top of two buffer access holes 31 communicated with the two ends of the common buffer flow channel 33 can be formed in the third structural layer 8 for the molecular detection array. Therefore, at this time, the buffer access hole 31 actually penetrates the first structural layer 6, the second structural layer 7 and the third structural layer 8, while the sample access hole 11 penetrates the second structural layer 7 and the third structural layer 8.

Step A5, forming an upper cover on the third structural layer, and forming a first interface and a second interface on the upper cover for the molecular detection array; here, the first interface is located above the sample access holes, and the second interface is located above the buffer access holes.

Figure 41:
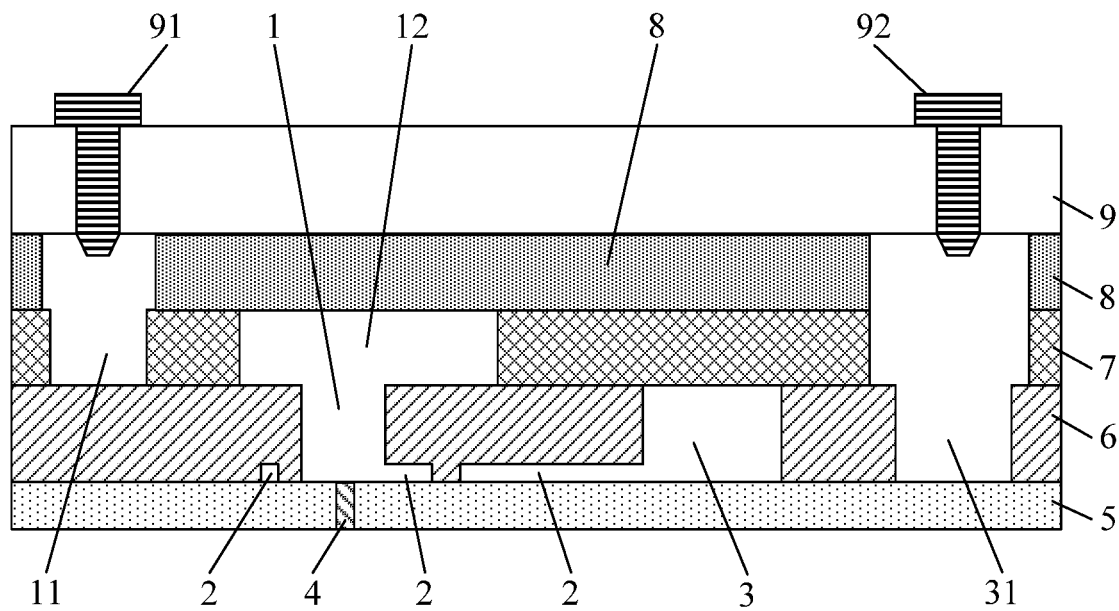
FIG. 41 is a seventh schematic diagram of the preparation process of the molecular detection chip in a specific embodiment of the present disclosure.

For example, as an example, as shown in FIG. 41, in a specific embodiment of the present disclosure, an upper cover 9 can be formed on the third structural layer 8.

For example, in a specific embodiment of the present disclosure, the material of the upper cover 9 can be some kind of plastic that can be bonded with photoresist, and can be manufactured by injection molding. For example, the material of the upper cover 9 may be polydimethylsiloxane (PDMS); the upper cover 9 may also be a multilayer structure with a PDMS layer.

For example, the upper cover 9 can be bonded with the third structural layer 8 in a certain way, and seal each sample access hole 11 and buffer access hole 31 to form a microfluidic chip. At the same time, two first interfaces 91 and two second interfaces 92 will be formed on the upper cover 9 for the molecular detection array, that is, one first interface 91 is arranged above each sample access hole 11, and one second port 92 is arranged above each buffer access hole 31, so as to communicate with the sample access hole 11 through the first port 91 and communicate with the buffer access hole 31 through the second port 92.

In addition, as an example, in a specific embodiment of the present disclosure, the first interface 91 can also be provided with a first driving electrode, and the second interface 92 can also be provided with a second driving electrode.

At this time, the above-mentioned first interface 91 and second interface 92 can be a structure that allows liquid to enter and driving electrodes to be connected, so that the corresponding liquid can be injected into the sample access hole 11 through the first interface 91, and a corresponding voltage can be applied to the liquid in the sample flow channel 12 through the first driving electrode in the first interface 91; and the corresponding liquid can be injected into the buffer access hole 31 through the second interface 92, and a corresponding voltage can be applied to the liquid in the buffer flow channel 3 through the second driving electrode in the second interface 92.

Through the above steps A1-A5, the required molecular detection chip can be prepared.

Figure 23:
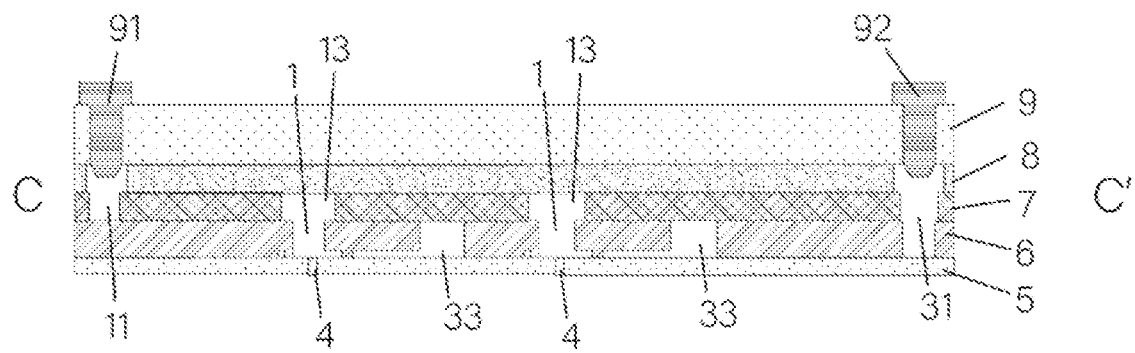
FIG. 23 is a second schematic cross-sectional view of CC' in FIG. 20.

In addition, in the technical solution of the present disclosure, the molecular detection chip prepared through the above-mentioned steps A1-A5 may include any cross-sectional molecular detection array as shown in the above-mentioned FIG. 23, FIG. 25 and FIG. 28.

In addition, in the technical solution of the present disclosure, a membrane layer 102 can be further formed at the junction of the single-hole liquid storage cavity 1 and the sample flow channel 12 of each molecular detection unit, and nanopores can be formed on the membrane layer 102.

For example, as an example, in a specific embodiment of the present disclosure, the method for preparing the molecular detection chip may further includes:

forming a membrane layer at the junction of the single-hole liquid storage cavity and the sample flow channel of each molecular detection unit, and forming nanopores on the membrane layers.

In the technical solution of the present disclosure, according to the positions of the single-hole liquid storage cavity 1 and the sample flow channel 12 of each molecular detection unit, a membrane layer 102 can be formed at the junction of the two; and then, a corresponding nanopore is formed on the membrane layer 102.

In addition, in the technical solutions of the present disclosure, various implementation methods can be used to form the membrane layer 102 and form nanopores on the membrane layer 102.

For example, as an example, in another specific embodiment of the present disclosure, the sample flow channel 12 and the buffer flow channel 3 can be injected and filled with buffer (a polar solution containing the required electrolyte) through the sample access hole 11 and the buffer access hole 31 respectively, the buffer will fill the sample flow channel 12, the buffer flow channel 3, the liquid resistance flow channel 2 and the single-hole liquid storage cavity 1. Then, a non-polar solution containing bipolar molecules (eg, phospholipid molecules) can be injected through the sample access hole 11. Due to the laminar flow characteristics of the liquid in the microchannel, the non-polar solution will only replace the buffer in the sample flow channel 12, but will not remove the buffer in the single-hole liquid storage cavity 1; and, since the two liquids have different polarities, the bipolar molecules will form a bipolar molecular film at the liquid interface at the junction of the single-hole liquid storage cavity 1 and the sample flow channel 12. Finally, the buffer is injected into the sample flow channel 12 through the sample access hole 11 to replace the non-polar solution. Similarly, due to the different polarities of the two liquids, bipolar molecules will form a membrane layer 102 at the junction of the single-hole liquid storage cavity 1 and the sample flow channel 12, for example, a bilayer film consisting of two layers of bipolar molecules.

After the above-mentioned membrane layer 102 is formed, nanopores will also be formed on the membrane layer 102. As an example, in a specific embodiment of the present disclosure, the above-mentioned method for setting nanopores (pore embedding method) may include the following process: first, inject a pore embedding solution containing porin into the sample flow channel 12 through the sample access hole 11 to replace the buffer originally present in the sample flow channel 12. Then apply corresponding voltages to the sample flow channel 12 and the buffer flow channel 3 respectively (for example, a voltage V3 can be applied to the sample flow channel 12 through the first interface 91, and a corresponding voltage V2 can be applied to the buffer flow channel 3 through the second interface 92), so as to form a potential difference on two sides of the membrane layer 102. This potential difference will change the permeability of the membrane layer, thereby forming nanometer-sized micropores on the surface of the membrane layer. At the same time, the porin in the pore embedding solution will move to the micropores under the action of the electric field due to its electrical properties, and finally be embedded in the micropores. Finally, a buffer is injected into the sample flow channel 12 through the sample access hole 11 to replace the pore embedding solution, which is convenient for subsequent storage. In actual operation, considering storage, transportation and other requirements, there may be a certain gap between the liquids in the sample flow channel 12 and the buffer flow channel 3.

Therefore, through the above steps, a membrane layer 102 can be formed at the junction of the single-hole liquid storage cavity 1 of the molecular detection unit and the sample flow channel 12, and nanopores can be formed on the membrane layer 102.

In addition, in the technical solution of the present disclosure, the positional relationship between the sample flow channel 12 and the single-hole liquid storage cavity 1 can also be pre-designed according to actual application requirements.

For example, as an example, in a specific embodiment of the present disclosure, the sample flow channel 12 can be arranged on the top of the single-hole liquid storage cavity 1, and the two are respectively arranged in different layers (the first structural layer 6 and the second structural layer 7), as shown in FIG. 2 and FIG. 4-FIG. 8.

At this time, the membrane layer 102 located at the junction of the single-hole liquid storage cavity 1 and the sample flow channel 12 can be constructed in a manner parallel to the substrate 5. For the specific construction method, reference may be made to the method for forming the membrane layer 102 with nanopores in the foregoing embodiments, which will not be repeated here.

For another example, as an example, in another specific embodiment of the present disclosure, the sample flow channel 12 may also be arranged on one side of the single-hole liquid storage cavity 1, that is, arranged in the same structural layer (the first structural layer 6).

At this time, the membrane layer 102 located at the junction of the single-hole liquid storage cavity 1 and the sample flow channel 12 can be constructed in a manner perpendicular to the substrate 5. For the specific construction method, reference may be made to the method for forming the membrane layer 102 with nanopores in the foregoing embodiments, which will not be repeated here.

In order to construct the membrane layer 102 in a manner perpendicular to the substrate 5, in the technical solution of the present disclosure, another method for preparing a molecular detection chip is also proposed.

Figure 46:
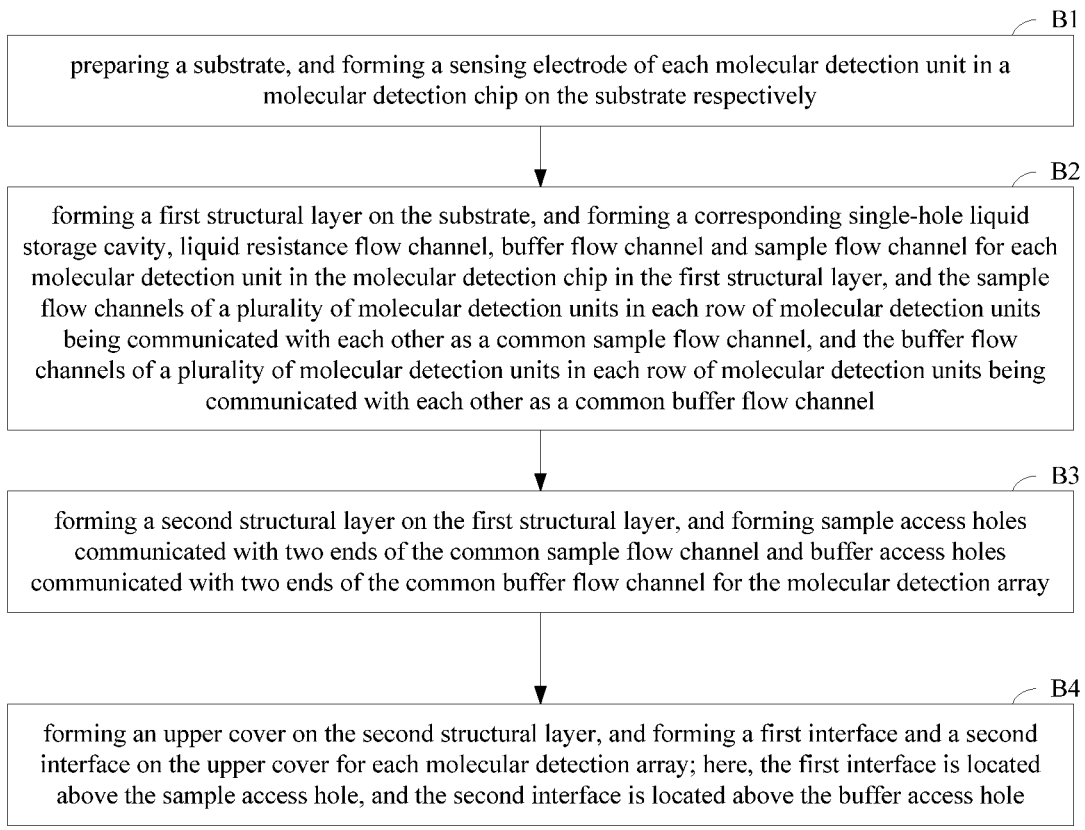
FIG. 46 is a schematic flowchart of a method for preparing a molecular detection chip in another specific embodiment of the present disclosure.

For example, as an example, as shown in FIG. 46, in a specific embodiment of the present disclosure, the method for preparing the above-mentioned molecular detection chip may include the following steps.

Step B1, preparing a substrate, and forming a sensing electrode of each molecular detection unit in a molecular detection chip on the substrate respectively.

Figure 47:
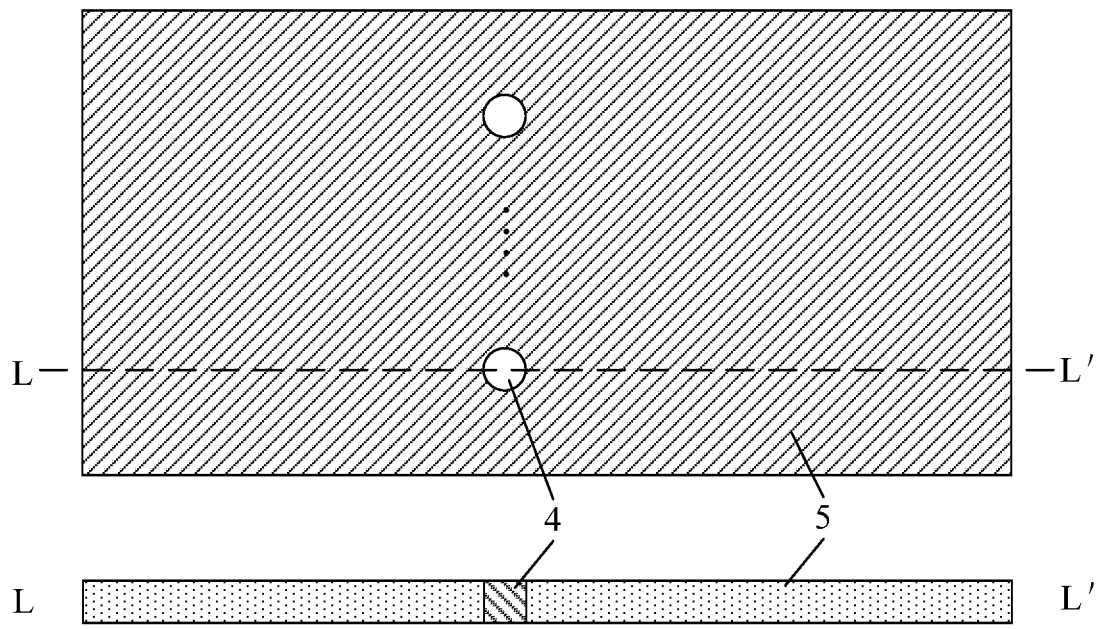
FIG. 47 is a first schematic diagram of the top view and cross-sectional view of the preparation process of the molecular detection chip in another specific embodiment of the present disclosure.

For example, as an example, as shown in FIG. 47 (in FIG. 47, the lower figure is a schematic cross-sectional view of LL' in the upper figure), in a specific embodiment of the present disclosure, step B1 can refer to the part of step A1 in the preceding embodiments, and will not be repeated here.

Step B2, forming a first structural layer on the substrate, and forming a corresponding single-hole liquid storage cavity, liquid resistance flow channel, buffer flow channel and sample flow channel for each molecular detection unit in the molecular detection chip in the first structural layer, and the sample flow channels of a plurality of molecular detection units in each row of molecular detection units being communicated with each other as a common sample flow channel, and the buffer flow channels of a plurality of molecular detection units in each row of molecular detection units being communicated with each other as a common buffer flow channel.

In this step, the first structural layer 6 will be formed on the substrate 5 first, and then the single-hole liquid storage cavity 1, the liquid resistance flow channel 2, the buffer flow channel 3 and the sample flow channel 12 will be formed in the first structural layer 6 for each molecular detection unit in the molecular detection chip; moreover, the sample flow channels 12 of multiple molecular detection units in each row of molecular detection units can also be connected to each other as a common sample flow channel, and the buffer flow channels 3 of the multiple molecular detection units in each row of molecular detection units can be connected to each other as a common buffer flow channel.

In addition, as an example, in a specific embodiment of the present disclosure, the bottom of two sample access holes 11 connected to two ends of the common sample flow channel can be further formed in the first structural layer 6 for the molecular detection array in the molecular detection chip, and the bottom of two buffer access holes 31 connected to two ends of the common buffer flow channel can be formed in the first structural layer 6 for the molecular detection array in the molecular detection chip.

In addition, in the technical solution of the present disclosure, various implementation manners may be used to realize the above step B2. The following will introduce the technical solutions of the present disclosure by taking one or several specific implementation manners as examples.

Figure 55:
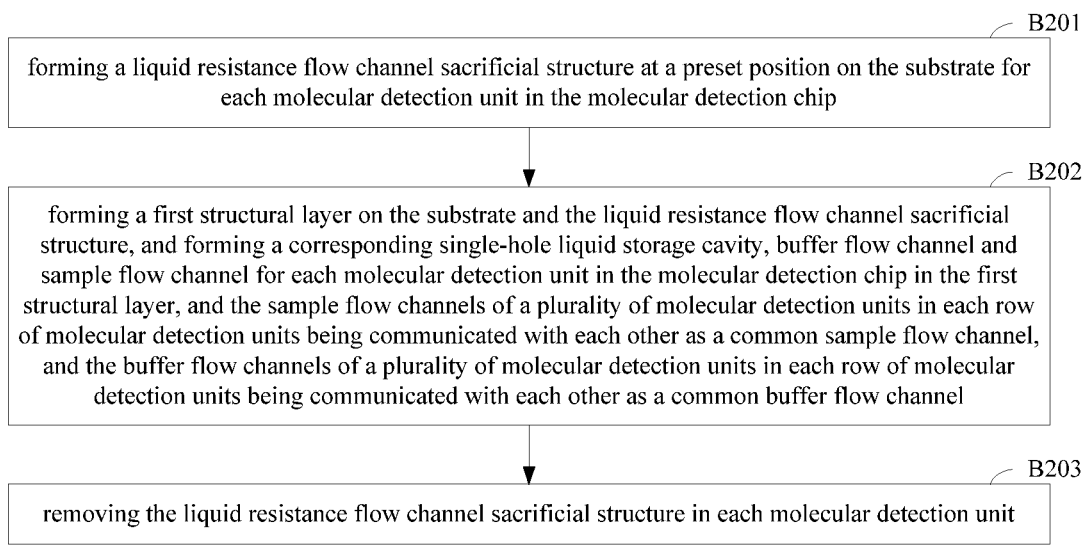
FIG. 55 is a schematic flowchart of a method for preparing a molecular detection chip in another specific embodiment of the present disclosure.

For example, as an example, as shown in FIG. 55, in a specific embodiment of the present disclosure, the above step B2 may include the following steps.

Step B201, forming a liquid resistance flow channel sacrificial structure at a preset position on the substrate for each molecular detection unit in the molecular detection chip.

Figure 48:
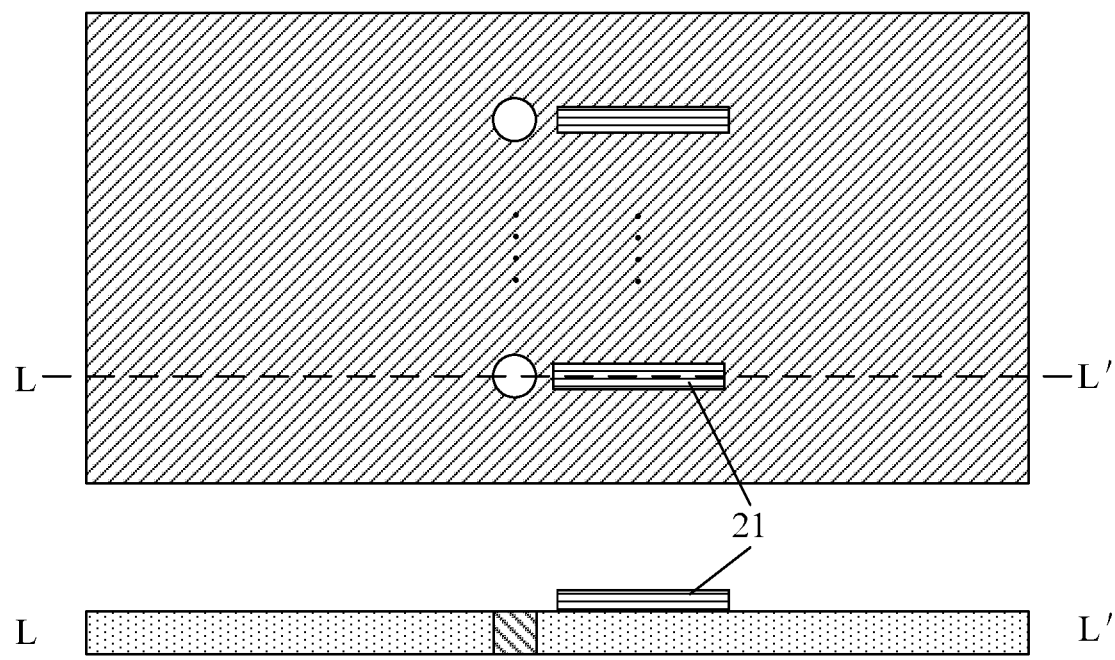
FIG. 48 is a second schematic diagram of the top view and cross-sectional view of the preparation process of the molecular detection chip in another specific embodiment of the present disclosure.

For example, as an example, as shown in FIG. 48 (in FIG. 48, the lower figure is a schematic cross-sectional view of LL' in the upper figure), in a specific embodiment of the present disclosure, step B201 can refer to the part of step A201 in the preceding embodiments, and will not be repeated here.

Step B202, forming a first structural layer on the substrate and the liquid resistance flow channel sacrificial structure, and forming a corresponding single-hole liquid storage cavity, buffer flow channel and sample flow channel for each molecular detection unit in the molecular detection chip in the first structural layer, and the sample flow channels of a plurality of molecular detection units in each row of molecular detection units being communicated with each other as a common sample flow channel, and the buffer flow channels of a plurality of molecular detection units in each row of molecular detection units being communicated with each other as a common buffer flow channel.

Figure 49:
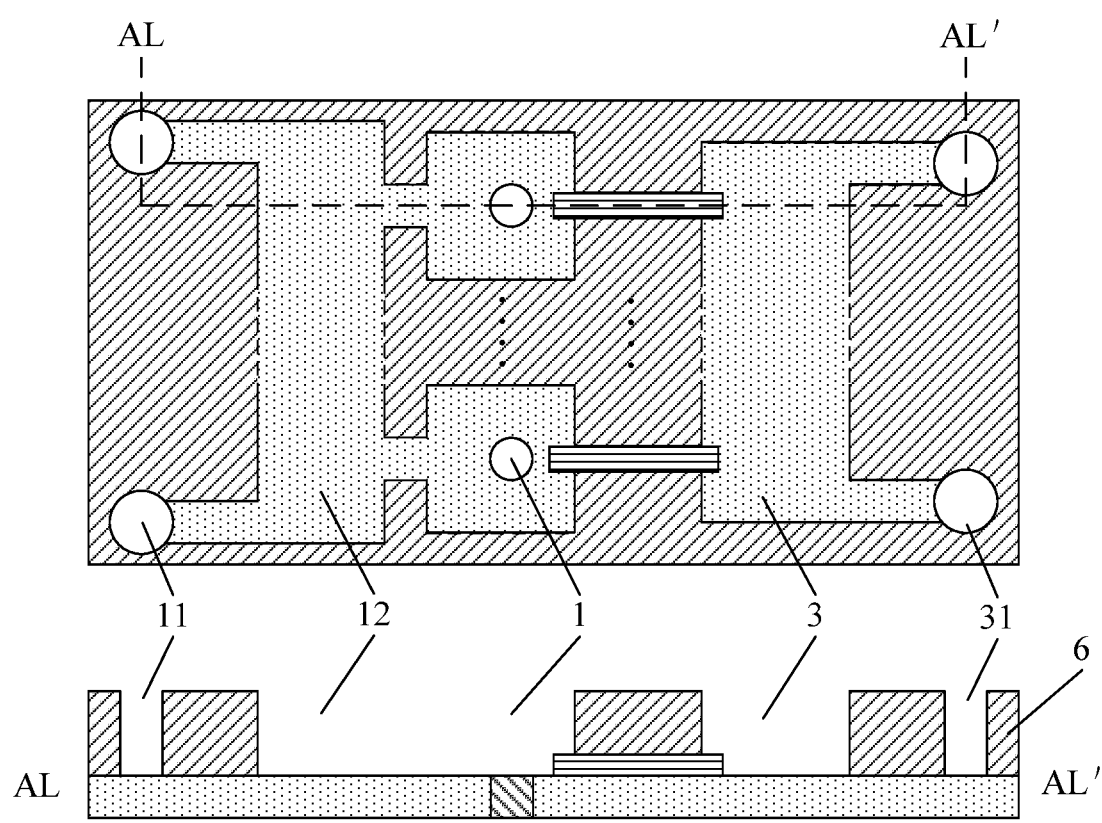
FIG. 49 is a third schematic diagram of the top view and cross-sectional view of the preparation process of the molecular detection chip in another specific embodiment of the present disclosure.

For example, as an example, as shown in FIG. 49 (in FIG. 49, the lower figure is a schematic cross-sectional view of ALAL' in the upper figure), in a specific embodiment of the present disclosure, for each molecular detection chip in the molecular detection chip unit, the first structural layer 6 covering the substrate 5 and the liquid resistance flow channel sacrificial structure 21 can be formed through some kind of material deposition process (for example, physical vapor deposition or chemical vapor deposition, etc.); and then, some kind of pattern transfer method (for example, photolithography, etc.) and some kind of etching process (for example, reactive ion etching, etc.) can be used to form the single-hole liquid storage cavity 1, the buffer flow channel 3 and the sample flow channel 12 of each molecular detection unit in the first structural layer 6, so that the single-hole liquid storage cavity 1 communicates with the sample flow channel 12. The sample flow channel 12 is located on one side of the single-hole liquid storage cavity 1 (for example, it can be located on the outside of the single-hole liquid storage cavity 1, that is, the side of the single-hole liquid storage cavity 1 away from the buffer flow channel 3); moreover, the sample flow channels 12 of multiple molecular detection units in each row of molecular detection units can also be connected to each other as a common sample flow channels, and the buffer flow channels 3 of multiple molecular detection units in each row of molecular detection units can be connected to each other as a common buffer flow channel.

In addition, as an example, in a specific embodiment of the present disclosure, the bottom of two sample access holes 11 connected to two ends of the common sample flow channel can be further formed in the first structural layer 6 for the molecular detection array in the molecular detection chip, and the bottom of two buffer access holes 31 connected to two ends of the common buffer flow channel can be formed in the first structural layer 6 for the molecular detection array in the molecular detection chip.

In addition, as an example, as shown in FIG. 49, in a specific embodiment of the present disclosure, since the sample flow channel 12 is arranged on one side of the single-hole liquid storage cavity 1, the side wall of the single-hole liquid storage cavity 1 can form a C-shaped structure, and an opening is provided on the side wall of the C-shaped structure close to the sample flow channel 12, and the side wall provided with the opening is used to support the nanopore, so as to facilitate the formation of a membrane layer 102 with nanopores at the junction of the single-hole liquid storage cavity 1 and the sample flow channel 12 using the film forming and pore embedding process based on microfluidic principle and polar/non-polar solvent interface effect in subsequent steps. The opening in the side wall defines the pore size where the membrane can be formed, which allows reducing the size and area of the membrane to reduce the capacitance of the membrane and increase the stability of the membrane.

In addition, the side wall of the C-shaped structure close to the buffer flow channel 3 can be connected with the liquid resistance flow channel sacrificial structure 21.

Step B203, removing the liquid resistance flow channel sacrificial structure in each molecular detection unit.

Figure 50:
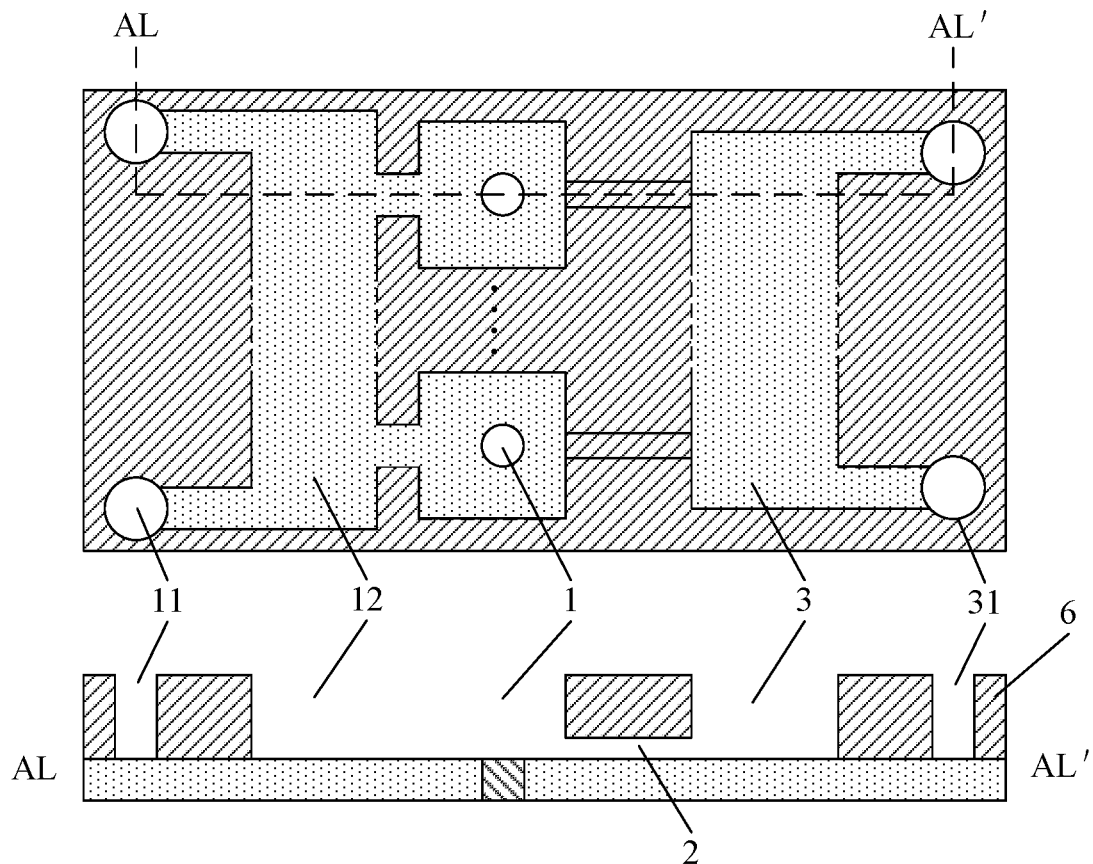
FIG. 50 is a fourth schematic diagram of the top view and cross-sectional view of the preparation process of the molecular detection chip in another specific embodiment of the present disclosure.

For example, as an example, as shown in FIG. 50 (in FIG. 50, the lower figure is a schematic cross-sectional view of ALAL' in the upper figure), in a specific embodiment of the present disclosure, step B203 can refer to the part of step A203 in the preceding embodiments, and will not be repeated here.

After the liquid resistance flow channel sacrificial structure 21 is removed, the liquid resistance flow channel 2 connecting the single-hole liquid storage cavity 1 and the buffer flow channel 3 can be formed, so that two sets of microchannel systems (the sample microchannel system and the buffer microchannel system) can be connected.

Through the above-mentioned steps B201~B203, the above-mentioned first structural layer 6 can be formed, and the single-hole liquid storage cavity 1, the liquid resistance flow channel 2, the buffer flow channel 3 and sample flow channel 12 of each molecular detection unit in the molecular detection chip can be formed in the first structural layer 6, and the sample flow channels 12 of multiple molecular detection units in each row of molecular detection units communicate with each other to form a common sample flow channel, and the buffer flow channels 3 of multiple molecular detection units in each row of molecular detection units communicate with each other as a common buffer flow channel. In addition, the bottoms of the two sample access holes 11 communicating with two ends of the common sample flow channel and the two bottoms of the two buffer access holes 31 communicating with two ends of the common buffer flow channel can be further formed in the first structural layer 6 for the molecular detection array.

Step B3, forming a second structural layer on the first structural layer, and forming sample access holes communicated with two ends of the common sample flow channel and forming buffer access holes communicated with two ends of the common buffer flow channel for the molecular detection array.

In the technical solution of the present disclosure, for the molecular detection array in the molecular detection chip, the second structural layer 7 can be formed on the first structural layer 6 through a corresponding semiconductor process (for example, some kind of bonding, combination or dry film process, etc.); then, according to the needs of the actual application scenario, various required structures are formed in the second structural layer 7.

Figure 51:
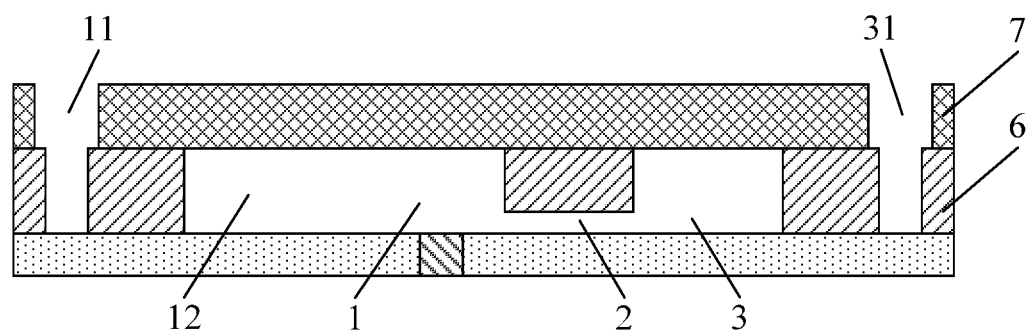
FIG. 51 is a fifth schematic diagram of the cross-sectional view of the preparation process of the molecular detection chip in another specific embodiment of the present disclosure.

For example, as an example, as shown in FIG. 51, in a specific embodiment of the present disclosure, for the molecular detection array in the molecular detection chip, the corresponding semiconductor process (for example, some kind of bonding, combination or dry film process, etc.) can be used to etc.) can be used to form the second structural layer 7 on the first structural layer 6. The second structural layer 7 covers the top of the common buffer flow channel, the common sample flow channel, the buffer flow channel 3 and the sample flow channel 12, so as to seal the common buffer flow channel, the common sample flow channel, the buffer flow channel 3 and the sample flow channel 12, so as to realize the overall sealing of the common buffer flow channel, the common sample flow channel, the buffer flow channel 3 and the sample flow channel 12. At this time, the single-hole liquid storage cavity 1 and the buffer flow channel 3 can only be connected through the liquid resistance flow channel 2 structurally.

In addition, a sample access hole connected to two ends of the common sample flow channel and a buffer access hole connected to two ends of the common buffer flow channel can also be formed in the second structural layer for the molecular detection array.

For example, as an example, in a specific embodiment of the present disclosure, the upper parts of the two sample access holes 11 communicating with the two ends of the common sample flow channel can be further formed in the second structural layer 7 for the molecular detection array, the upper parts of the two buffer access holes 31 communicating with the two ends of the common buffer flow channel can be formed in the second structural layer 7 for the molecular detection array. Therefore, at this time, both the sample access hole 11 and the buffer access hole 31 actually penetrate the first structural layer 6 and the second structural layer 7.

Step B4, forming an upper cover on the second structural layer, and forming a first interface and a second interface on the upper cover for each molecular detection array; here, the first interface is located above the sample access hole, and the second interface is located above the buffer access hole.

For example, as an example, in a specific embodiment of the present disclosure, step B4 can refer to the part of step A5 in the preceding embodiments, and will not be repeated here.

Therefore, the above-mentioned molecular detection chip in the present disclosure can be prepared through the above-mentioned steps B1-B4.

In addition, in the technical solution of the present disclosure, a membrane layer 102 can be further formed at the junction of the single-hole liquid storage cavity 1 and the sample flow channel 12 of each molecular detection unit, and nanopores can be formed on the membrane layer 102.

For example, as an example, in a specific embodiment of the present disclosure, the method for preparing the molecular detection chip may further include:

forming a membrane layer at the junction of the single-hole liquid storage cavity and the sample flow channel of each molecular detection unit, and forming nanopores on the membrane layers.

Figure 52:
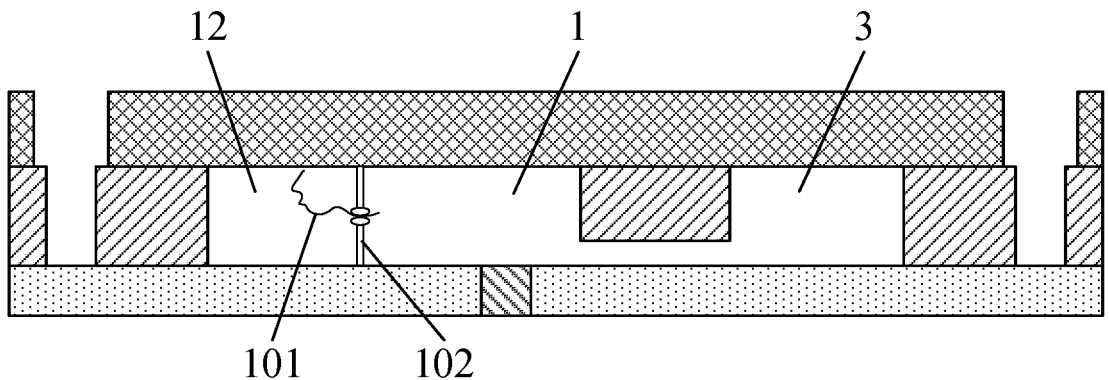
FIG. 52 is a sixth schematic diagram of the cross-sectional view of the preparation process of the molecular detection chip in another specific embodiment of the present disclosure.

For example, as an example, as shown in FIG. 52, in a specific embodiment of the present disclosure, the above can refer to the part of step in the preceding embodiments, and will not be repeated here.

In this step, the above-mentioned membrane layer 102 can be constructed in a manner perpendicular to the substrate 5. Therefore, the above-mentioned membrane layer 102 can be formed in the side wall opening between the single-hole liquid storage cavity 1 and the sample flow channel 12 by a corresponding film forming and pore embedding method, and corresponding nanopores can be formed on the membrane layer 102.

The effect of this preparation method is that a cantilever structure can be simply fabricated between the single-hole liquid storage cavity 1 and the sample flow channel 12.

In summary, in the technical solution of the present disclosure, since two sets of independent microchannel systems are constructed by using multi-layer flow channels, and interconnection can be achieved by removing the liquid resistance flow channel sacrificial structure between the two systems before the final application, to realize the fabrication of the liquid resistance flow channel and the buffer flow channel is completed on the same side of the substrate, the single-hole liquid storage cavity, the liquid resistance flow channel, the buffer flow channel and the sample flow channel are all located on the same side of the substrate, so the liquid resistance flow channel and the buffer flow channel can be constructed on the same surface of the substrate, which can effectively improve the chip production efficiency based on the voltage sequencing method, and further improve the flux of the nanopore sequencing device.

In addition, in the technical scheme of the present disclosure, since the sample flow channel and the buffer flow channel are isolated from each other, different voltages can be applied to different liquids in the two flow channels, thereby ensuring the realization of the basic principle of voltage sequencing.

In addition, the above separated two flow channels can also greatly reduce cross-contamination and electric leakage between samples, and improve the signal-to-noise ratio of the signal.

The above descriptions are only preferred embodiments of the present disclosure, and are not intended to limit the present disclosure. Any modifications, equivalent replacements, improvements, etc. made within the spirit and principles of the present disclosure shall be included in the present disclosure within the scope of protection.

What is claimed is:

1. A molecular detection unit, comprising: a single-hole liquid storage cavity, a liquid resistance flow channel, a buffer flow channel, a sensing electrode, a substrate, a first structural layer, a second structural layer, and a sample flow channel; wherein the first structural layer is arranged on a top of the substrate;

the single-hole liquid storage cavity and the buffer flow channel are arranged in the first structural layer and are independent of each other;

the liquid resistance flow channel is arranged in the first structural layer; two ends of the liquid resistance flow channel are respectively communicated with the single-hole liquid storage cavity and the buffer flow channel;

the second structural layer is arranged on a top of the first structural layer and covers a top of the buffer flow channel;

the sample flow channel is communicated with the single-hole liquid storage cavity; and the sensing electrode is arranged in the substrate; one end of the sensing electrode is connected to the single-hole liquid storage cavity for detecting a voltage applied to a side of the single-hole liquid storage cavity.

2. The molecular detection unit according to claim 1, further comprising: a membrane layer; wherein
the membrane layer is arranged at the junction of the sample flow channel and the single-hole liquid storage cavity; and
the membrane layer is provided with a nanopore.

3. The molecular detection unit according to claim 1, wherein
the sample flow channel is arranged in the second structural layer and is located on a top of the single-hole liquid storage cavity.

4. The molecular detection unit according to claim 1, further comprising: two sample access holes and two buffer access holes; wherein
the two sample access holes are respectively communicated with two ends of the sample flow channel; and
the two buffer access holes are respectively communicated with two ends of the buffer flow channel.

5. The molecular detection unit according to claim 4, wherein
the sample access holes penetrate through the second structural layer to communicate with the sample flow channel; and
the buffer access holes penetrate through the second structural layer and the first structural layer to communicate with the buffer flow channel.

6. The molecular detection unit according to claim 5, further comprising: a third structural layer; wherein
the third structural layer is arranged on a top of the second structural layer; and
a top of the sample access holes and a top of the buffer access holes are arranged in the third structural layer.

7. The molecular detection unit according to claim 6, further comprising: an upper cover, a first interface and a second interface; wherein
the upper cover is arranged on the third structural layer and covers tops of the sample access holes and the buffer access holes;
the top of each sample access hole is provided with the first interface penetrating through the upper cover; and
the top of each buffer access hole is provided with the second interface penetrating through the upper cover.

8. The molecular detection unit according to claim 7, wherein the molecular detection unit further comprises: a first driving electrode and a second driving electrode;
the first driving electrode is arranged in each first interface, and the second driving electrode is arranged in each second interface.

9. A molecular detection chip, comprising: a molecular detection array; wherein
the molecular detection array comprises at least one row of molecular detection units; each row of molecular detection units comprises a plurality of molecular detection units according to claim 1;
the sample flow channels of the plurality of molecular detection units in each row of molecular detection units are communicated with each other as a common sample flow channel; and
the buffer flow channels of the plurality of molecular detection units in each row of molecular detection units are communicated with each other as a common buffer flow channel.

10. The molecular detection chip according to claim 9, wherein
the number of the common sample flow channels in the molecular detection array is equal to the number of rows of molecular detection units in the molecular detection array.

11. The molecular detection chip according to claim 10, wherein
one common sample flow channel is shared by the plurality of molecular detection units in one row of molecular detection units.

12. The molecular detection chip according to claim 9, wherein
when the molecular detection array comprises a plurality of rows of molecular detection units, the number of the common sample flow channels in the molecular detection array is less than the number of rows of molecular detection units in the molecular detection array.

13. The molecular detection chip according to claim 12, wherein
one common sample flow channel is shared by the plurality of molecular detection units in at least two rows of molecular detection units.

14. The molecular detection chip according to claim 9, wherein
the number of the common buffer flow channels in the molecular detection array is equal to the number of rows of molecular detection units in the molecular detection array.

15. The molecular detection chip according to claim 14, wherein
one common buffer flow channel is shared by the plurality of molecular detection units in one row of molecular detection units.

16. The molecular detection chip according to claim 9, wherein
when the molecular detection array comprises a plurality of rows of molecular detection units, the number of the common buffer flow channels in the molecular detection array is less than the number of rows of molecular detection units in the molecular detection array.

17. The molecular detection chip according to claim 16, wherein
one common buffer flow channel is shared by the plurality of molecular detection units in two adjacent rows of molecular detection units.

18. The molecular detection chip according to claim 9, further comprising: two sample access holes and two buffer access holes; wherein
two ends of the common sample flow channel are respectively communicated with two sample access holes; and
two ends of the common buffer flow channel are respectively communicated with two buffer access holes.

19. A method for preparing a molecular detection chip, comprising:
preparing a substrate, and forming a sensing electrode of each molecular detection unit in a molecular detection chip on the substrate respectively; the sensing electrode is used to detect a voltage applied to a side of the single-hole liquid storage cavity;
forming a first structural layer on the substrate, and forming a corresponding single-hole liquid storage cavity, liquid resistance flow channel and buffer flow channel for each molecular detection unit in the molecular detection chip in the first structural layer, and the buffer flow channels of a plurality of molecular detection units in each row of molecular detection units being communicated with each other as a common buffer flow channel;

for a molecular detection array, forming a second structural layer on the first structural layer, sealing the common buffer flow channel and the buffer flow channel of each molecular detection unit, and forming a sample flow channel for each molecular detection unit in the second structural layer, and the sample flow channels of a plurality of molecular detection units in each row of molecular detection units being communicated with each other as a common sample flow channel;

forming a third structural layer on the second structural layer, and forming sample access holes communicated with two ends of the common sample flow channel and forming buffer access holes communicated with two ends of the common buffer flow channel for the molecular detection array; and forming an upper cover on the third structural layer, and forming a first interface and a second interface on the upper cover for the molecular detection array; wherein, the first interface is located above the sample access holes, and the second interface is located above the buffer access holes.

20. The method according to claim 19, wherein forming a first structural layer on the substrate, and forming a corresponding single-hole liquid storage cavity, liquid resistance flow channel and buffer flow channel for each molecular detection unit in the molecular detection chip in the first structural layer; and the buffer flow channels of a plurality of molecular detection units in each row of molecular detection units being communicated with each other as a common buffer flow channel comprises:

forming a liquid resistance flow channel sacrificial structure at a preset position on the substrate for each molecular detection unit in the molecular detection chip;

forming the first structural layer on the substrate and the liquid resistance flow channel sacrificial structure, and forming the corresponding single-hole liquid storage cavity and buffer flow channel for each molecular detection unit in the molecular detection chip in the first structural layer, and the buffer flow channels of the plurality of molecular detection units in each row of molecular detection units being communicated with each other as a common buffer flow channel; and removing the liquid resistance flow channel sacrificial structure in each molecular detection unit.

\* \* \* \* \*